United States Patent
San Martin et al.

(10) Patent No.: US 10,487,643 B2
(45) Date of Patent: Nov. 26, 2019

(54) TWO-DIMENSIONAL IMAGING WITH MULTI-STAGE PROCESSING

(71) Applicant: Halliburton Energy Services, Inc., Houston, TX (US)

(72) Inventors: Luis Emilio San Martin, Houston, TX (US); Reza Khalaj Amineh, Houston, TX (US); Burkay Donderici, Pittsford, NY (US)

(73) Assignee: Halliburton Energy Services, Inc., Houston, TX (US)

( * ) Notice: Subject to any disclaimer, the term of this patent is extended or adjusted under 35 U.S.C. 154(b) by 27 days.

(21) Appl. No.: 15/766,198

(22) PCT Filed: Nov. 12, 2015

(86) PCT No.: PCT/US2015/060388
§ 371 (c)(1),
(2) Date: Apr. 5, 2018

(87) PCT Pub. No.: WO2017/082912
PCT Pub. Date: May 18, 2017

(65) Prior Publication Data
US 2018/0306023 A1   Oct. 25, 2018

(51) Int. Cl.
*E21B 47/00* (2012.01)
*G01N 27/82* (2006.01)
*G01B 7/06* (2006.01)
*E21B 47/12* (2012.01)

(52) U.S. Cl.
CPC ...... *E21B 47/0006* (2013.01); *E21B 47/0002* (2013.01); *G01B 7/10* (2013.01); *G01N 27/82* (2013.01); *E21B 47/122* (2013.01)

(58) Field of Classification Search
None
See application file for complete search history.

(56) References Cited

U.S. PATENT DOCUMENTS

| | | | | |
|---|---|---|---|---|
| 5,270,647 A | * | 12/1993 | Beissner | G01V 3/08 324/220 |
| 2002/0194916 A1 | * | 12/2002 | Yamada | G01B 17/025 73/627 |
| 2013/0193953 A1 | | 8/2013 | Yarbro et al. | |

FOREIGN PATENT DOCUMENTS

WO    2015050840 A1    4/2015

OTHER PUBLICATIONS

"International Application Serial No. PCT/US2015/060388, International Search Report dated Aug. 22, 2016", 3 pgs.
"International Application Serial No. PCT/US2015/060388, Written Opinion dated Aug. 22, 2016", 9 pgs.

* cited by examiner

*Primary Examiner* — Clayton E. LaBalle
*Assistant Examiner* — Jas A Sanghera
(74) *Attorney, Agent, or Firm* — Gilliam IP PLLC

(57) ABSTRACT

Apparatus and methods to image pipes of a multi-pipe structure can be implemented in a variety of applications. The multi-pipe structure may be associated with a well site, such as a multi-casing structure for a production well. Individual pipes of the multi-pipe structure may be investigated in a multi-stage process using delta-like responses, where previous stages provide inputs to subsequent stages. The results of multi-stage processing can be used to image defects in the multi-pipe structure.

20 Claims, 9 Drawing Sheets

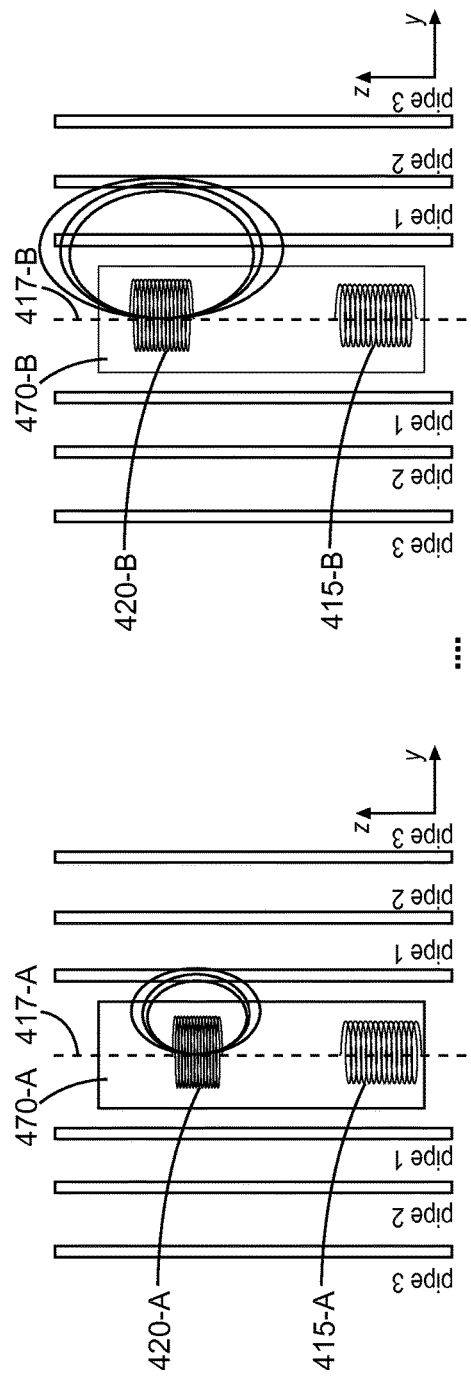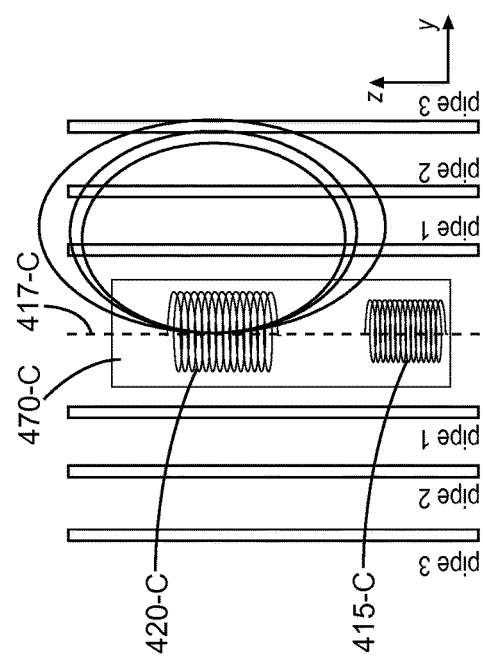

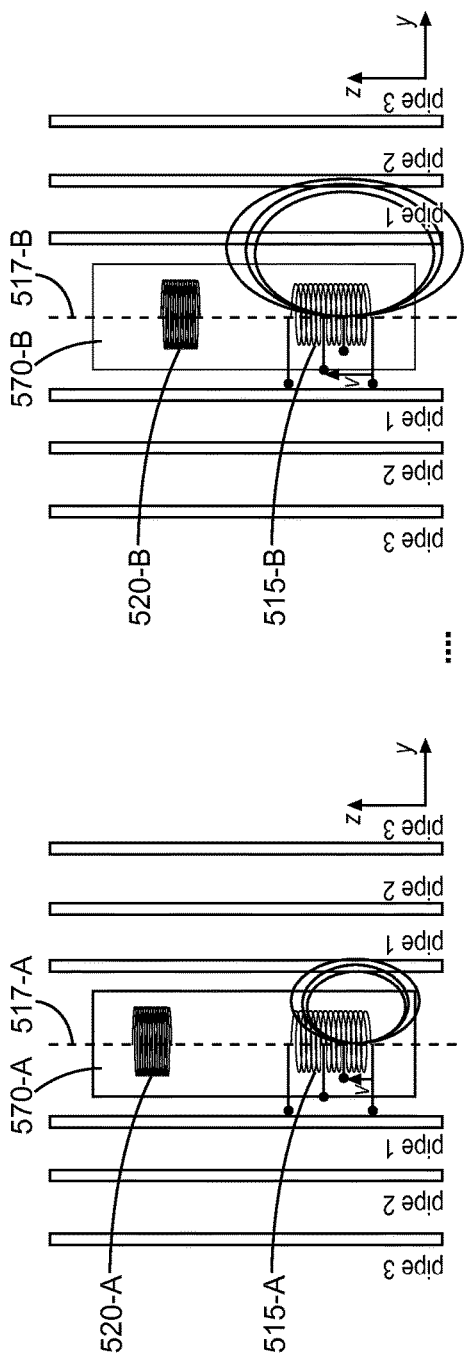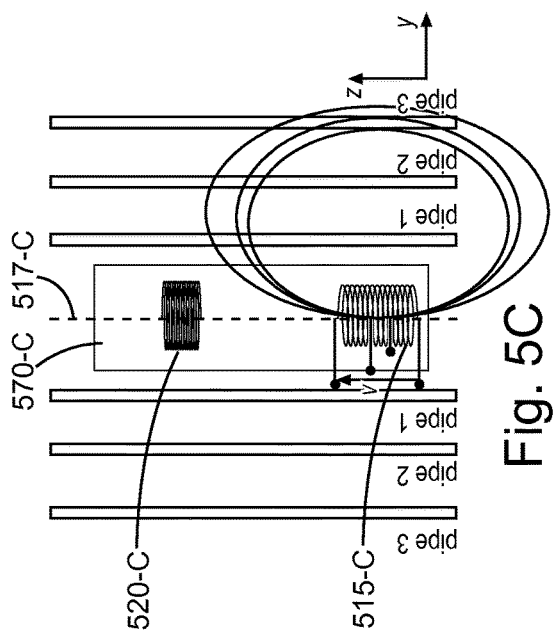

US 10,487,643 B2

TWO-DIMENSIONAL IMAGING WITH MULTI-STAGE PROCESSING

TECHNICAL FIELD

The present invention relates generally to apparatus and methods with respect to measurements related to oil and gas exploration.

BACKGROUND

Monitoring the condition of production tubing, different casing strings, joints, collars, filters, packers and perforations is crucial in oil and gas field operations. Electromagnetic (EM) techniques are common means to evaluate these components. EM sensing provides continuous, in situ measurements of the integrity of tubing/casing. EM technologies developed for such monitoring applications can be categorized into two groups: frequency-domain techniques and time-domain techniques. In frequency-domain techniques, typically, measurements are performed over a range of frequencies, low frequency and a high frequency within this range, to perform characterization of the internal and external features of the casing, respectively. Proper analysis of the responses can determine metal losses with better resolutions and also improve the robustness of the characterization process to noise. The usefulness of such measurements may be related to the precision or quality of the information and the presentation of the data derived from such measurements.

BRIEF DESCRIPTION OF THE DRAWINGS

FIGS. 4A-4C are schematic representations of receiving responses up to the $1^{st}$, $2^{nd}$ and $3^{rd}$ pipes of a multi-pipe arrangement having at least three pipes by using receivers with variable sizes or numbers of turns of coils, in accordance with various embodiments.

FIGS. 5A-5C are schematic representations of excitation of fields with variable strengths to excite up to the $1^{st}$, $2^{nd}$, and $3^{rd}$ pipes by employing a tapped transmitter coil, in accordance with various embodiments.

DETAILED DESCRIPTION

Figure 1:
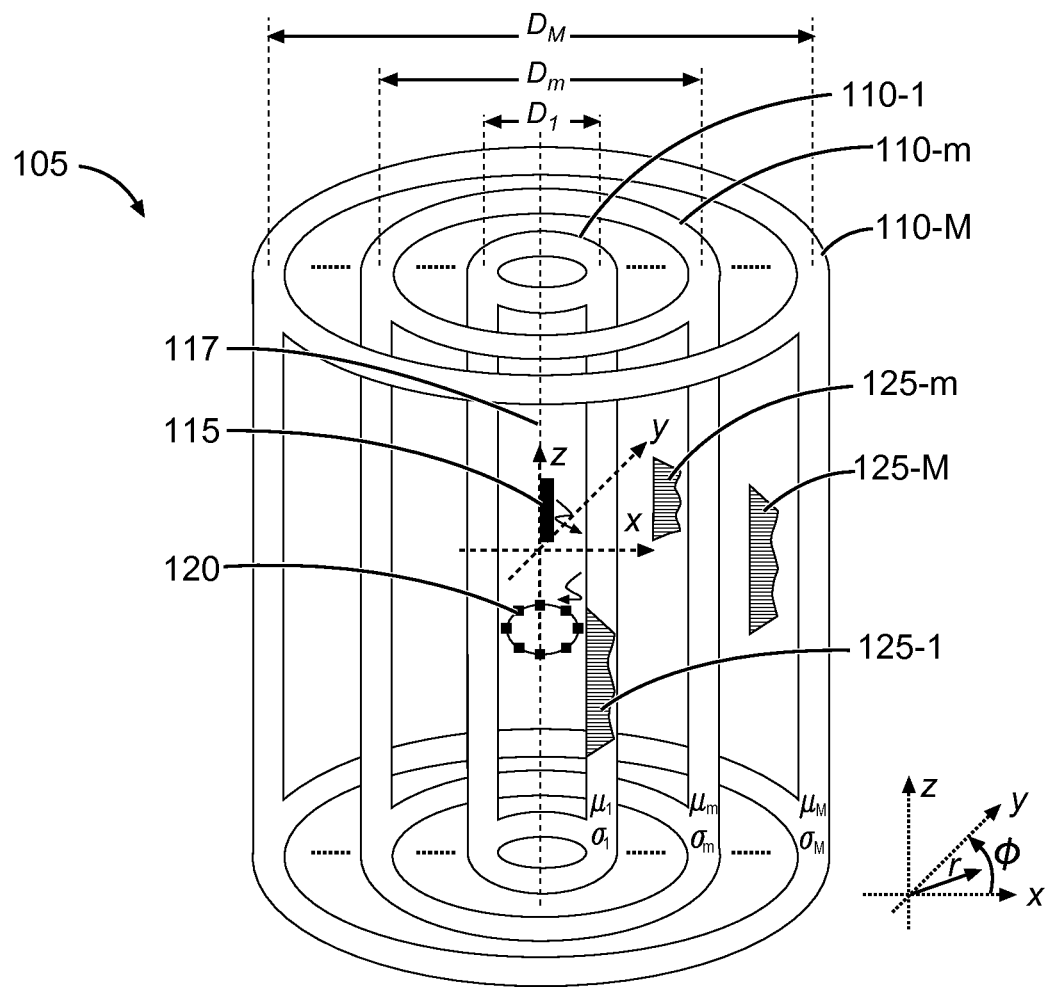
FIG. 1 is a schematic representation of an example setup of a multi-pipe structure to which an embodiment of holographic imaging can be applied, in accordance with various embodiments.

The following detailed description refers to the accompanying drawings that show, by way of illustration and not limitation, various embodiments in which the invention may be practiced. These embodiments are described in sufficient detail to enable those skilled in the art to practice these and other embodiments. Other embodiments may be utilized, and structural, logical, and electrical changes may be made to these embodiments. The various embodiments are not necessarily mutually exclusive, as some embodiments can be combined with one or more other embodiments to form new embodiments. The following detailed description is, therefore, not to be taken in a limiting sense.

Since EM sensing can provide continuous, in situ measurements of the integrity of tubing/casing, there has been considerable interest in using EM in cased borehole monitoring applications. However, the available tools commonly do not employ elaborate visualization of the results for the evaluation of multiple pipes. One corrosion inspection tool, for example, provides estimates of the total thickness of the casings, employing multiple frequency-domain data acquisitions and interpretations and using an inversion process. However, this tool has not been tailored for the evaluation of individual casings. Other corrosion inspection tools analyze the time-domain decay response to characterize the tubing plus casing, with an inversion process based on comparison of measured response with simulated responses in a library for pre-known casings. The final results of these tools are in the form of estimated thickness values for these two pipes.

In various embodiments, a holographic two-dimensional (2D) imaging technique and a tool can be implemented that improves the resolution of defect evaluation. Such techniques and tools can lead to better resolution for monitoring of pipe condition, i.e., small dimensional features of flaws and metal losses can be resolved with better accuracy. While maintaining good resolution, larger illuminating sources or sensors can be employed, which can allow for monitoring multiple casings with larger outer diameters (ODs). By converting time-domain data to frequency domain and applying a multiple frequency holographic inversion algorithm, robustness to noise can be improved significantly, since approaches taught herein inherently include a low-pass filtering process. Inversion is a process of searching for a match between simulated data and measurements. Inversion operations can include a comparison of measurements to predictions of a forward model such that a value or spatial variation of a physical property can be determined. A forward model deals with calculating expected observed values with respect to an assumed model of casings with associated casing's properties and dimensions. Characterization of casings with better resolution can provide a more precise evaluation of these components and may ultimately lead to a significant positive impact on assessing and maintaining pipe integrity.

FIG. 1 is a schematic representation of an example setup of a multi-pipe structure to which an embodiment of holographic imaging can be applied. The reference labels $D_m$, $\mu_m$, and $\sigma_m$ denote the outer diameter of the m-th pipe, relative permeability of the m-th pipe, and conductivity of the m-th pipe, respectively. Herein, the term "pipe" is used to refer to pipes or casings. FIG. 1 is a schematic diagram of a transmitter 115 and a receiver 120 in a multi-pipe structure 105. The multi-pipe structure 105 may include pipes 110-1 . . . 110-m . . . 110-M. The multi-pipe structure 105 may be disposed in a borehole at a well site. Though, FIG. 1 shows three pipes (M=3), the multi-pipe structure 105 may include more or less than three pipes. Pipe 110-1 has a diameter, $D_1$, a magnetic permeability, $\mu_1$, and electrical conductivity, $\sigma_1$. Pipe 110-m has a diameter $D_m$, a magnetic permeability, $\mu_m$, and electrical conductivity, $\sigma_m$. Pipe 110-M has a diameter $D_M$, a magnetic permeability, $\mu_M$, and electrical conductivity, $\sigma_M$. Each of the pipes of the multi-pipe structure 105 may include one or more defects at different depths. A defect may be a void, corrosion, or combinations thereof. As a non-limiting example, FIG. 1 shows pipe 110-1 with defect 125-1, pipe 110-m with defect 125-m, and pipe 110-M with defect 125-M. The transmitter 115 and a receiver 120 can be operated to inspect the pipes of the multi-pipe structure 105 to determine if each of the pipes has defects and to image the results of the inspection of the multi-pipe structure 105.

Responses can be acquired from signals received from the pipes 110-1 . . . 110-m . . . 110-M of the multi-pipe structure 105 in response to transmission of a probe signal from the transmitter 115 operatively disposed within the multi-pipe structure 105. An inversion operation can be executed to operate on these responses. The dimensions of defects in the pipes 110-1 . . . 110-m . . . 110-M of the multi-pipe structure 105 can be estimated from the responses by employing a proper inversion algorithm.

The transmitter 115 is an excitation source that may include one or more transmitting devices. The receiver 120 may be structured as an array of receiving sensors. The receiver 120 may include an azimuthally distribution sensor array. The transmitter 115 and the receiver 120 may be realized by one or more types of electromagnetic sensors or magnetic sensors. The transmitter 115 and the receiver 120 may be arranged to probe the pipes 110-1 . . . 110-m . . . 110-M with the transmitter 115 and the receiver 120 disposed within the innermost pipe 110-1. Alternatively, the transmitter 115 and the receiver 120 may be arranged within a pipe different from the innermost pipe 110-1. The transmitter 115 and the receiver 120 can be moved along a longitudinal axis 117 of innermost pipe 110-1 to make measurements at different depths. Wireline arrangements, or other conventional conveyance techniques, can be used to dispose the transmitter 115 and the receiver 120 in the multi-pipe structure 105 below the earth's surface at a well site. Movement along the longitudinal axis 117 may be conducted within the multi-pipe structure 105 parallel to longitudinal axis 117. Alternatively, the transmitter 115 and the receiver 120 may be realized as a number of transmitters and receivers within the multi-pipe structure 105 disposed at different depths from the earth's surface.

With the receiver 120 realized as an azimuthally distribution sensor array, the sensors of the azimuthally distribution sensor array may be uniformly placed at equal angles in a plane forming a loop. The loop can be formed around the longitudinal axis 117. Alternatively, the sensors of the azimuthally distribution sensor array may be arranged at different angles from one sensor to its adjacent sensor.

A probe signal may be sent out from the transmitter 115. The characteristics of signals propagated back from pipes 110-1, 110-2 . . . 110-M of multi-pipe structure 105 can be based on the properties of the pipes 110-1, 110-2 . . . 110-M. A defect in a pipe in most cases can have properties such as magnetic permeability and electrical conductivity that are different from the non-defect portion of the pipe. Measurement of these signals can be processed to derive metal loss of each of the pipes 110-1, 110-2 . . . 110-M. The signals from the walls of the pipes can be processed to provide a visualization or image of the pipes, in which the regions between the walls of the pipes are background regions that are effectively transparent.

In various embodiments, the transmitter 115 and the receiver 120 can be structured and/or operated such that responses are received only from effectively exciting a selected one of the pipes 110-1 . . . 110-m . . . 110-M and exciting pipes that are located inner to the selected pipe. Pipes, from which signals are received, where the signals are too low in strength to be adequately processed, may be taken to effectively be non-excited pipes. These responses for the complete set of the pipes 110-1 . . . 110-2 . . . 110-M can be processed in a multi-stage process. With respect to the innermost pipe, for example pipe 110-1, the transmitter 115 and the receiver 120 can be structured and/or operated such that responses are effectively received only from the innermost pipe 110-1. A procedure of estimating the defect in the innermost pipe can include using a delta-like response to determine properties of the innermost pipe. The delta-like response being associated with a defect and can also be referred to as a delta-like defect response. With respect to the second innermost pipe, the transmitter 115 and the receiver 120 can be structured and/or operated such that responses are effectively received only from the innermost pipe 110-1 and the second innermost pipe. A procedure of estimating the defect in the second innermost pipe can include using a delta-like response and determined properties of the innermost pipe 110-1 to determine properties of the second innermost pipe. Each pipe 110-1 . . . 110-m, . . . , and 110-M of the multi-pipe structure 105 can be addressed individually in stages taking into consideration properties the pipes of the multi-pipe structure 105 previously determined. An image of the multi-pipe structure 105 can be generated using the estimated defect in each pipe 110-1 . . . 110-m, . . . , and 110-M of the multi-pipe structure 105.

Figure 2A:
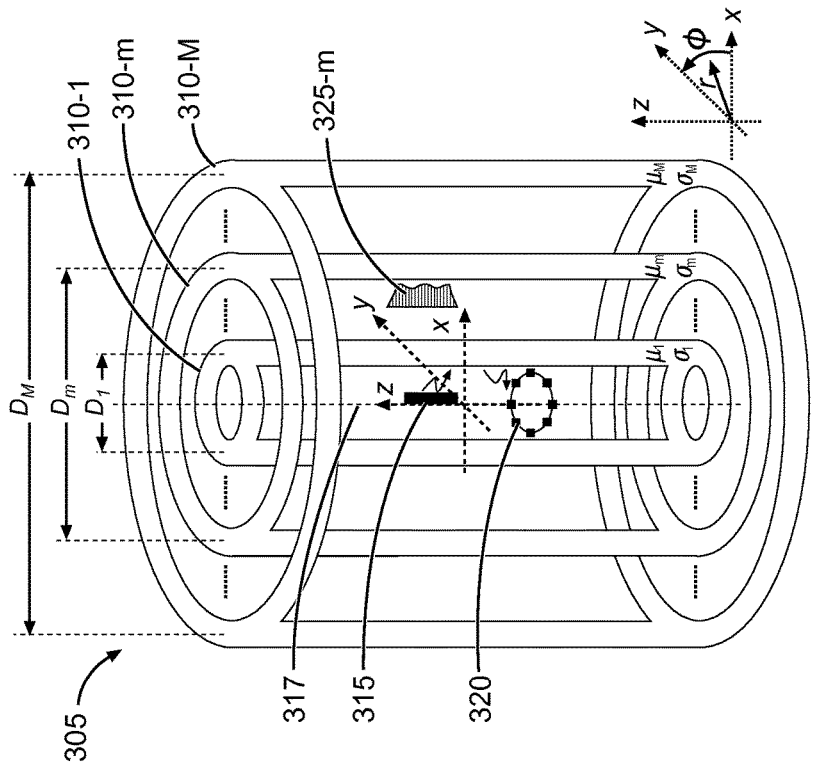
FIG. 2A is a schematic representation of an example linear measurement system with a small (delta-like) metal loss on the $m^{th}$ casing of a multiple-casing structure, in accordance with various embodiments.

In applying a holographic algorithm, the measurement system may be assumed linear. This assumption can be made based on the well-known Born approximation. FIG. 2A is a schematic representation of an example linear measurement system with a small (delta-like) metal loss 225-m on the $m^{th}$ casing of a multiple-casing structure 205, for example, at a well site. Here and in what follows, a loss that is just large enough to be detected by the sensors is called a small delta-like metal loss. For clarity, and without loss of generality, a small delta-like metal loss can be defined for a pipe of outer diameter (OD) D, as an azimuthally symmetric loss of length L and thickness $\delta$, so that the OD at the section with loss is $D-2\delta$. What is important in the definition of this delta-like defect is that the loss is small and at the limit of detectability. The shape of the loss could be different and the arguments that follow would apply with minimal modification to losses of different shape, such as a cut, for example. The methods taught herein are applicable to any kind of small defect with minor modifications, which can be understood to follow from these methods. FIG. 2A shows a transmitter 215 and a receiver 220 along a longitudinal axis 217 in the multi-casing structure 205, similar to FIG. 1. The multi-casing structure 205 may include casings 210-1 . . . 210-m . . . 210-M. Though, FIG. 2A shows three casings (M=3), the multi-casing structure 205 may include more or less than three casings. Casing 210-1 has a diameter, $D_1$, a magnetic permeability, $\mu_1$, and electrical conductivity, $\sigma_1$. Casing 210-m has a diameter $D_m$, a magnetic permeability, $\mu_m$, and electrical conductivity, $\sigma_m$. Casing 210-M has a diameter $D_M$, a magnetic permeability, $\mu M$, and electrical conductivity, $\sigma M$. As a non-limiting example, FIG. 2A shows casing 210-m with delta- like defect 225-m. The transmitter 215 and a receiver 220 can be operated to inspect the casings of the multi-casing structure 205 to determine a response to excitation of casing 210-m and properties of casing 210-m associated with the delta-like defect 225-m.

Figure 3A:
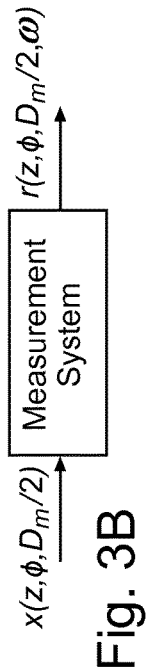
FIG. 3A is a representation of a linear measurement system with a delta-like metal loss, in accordance with various embodiments.

For a linear measurement system, once the measured response to a delta-like metal loss region is attained, the measured response for any other investigated metal loss region can be computed. If there is a small, but measurable, metal loss in the $m^{th}$ casing at $z=0$ and $\phi=0$ as shown in FIG. 2A, this metal loss can be approximated with a Dirac delta function at radial distance of $D_m/2$, where $D_m$ is the diameter of the $m^{th}$ casing. This Dirac delta function can be represented as $\delta(z, \phi, D_m/2)$, where z is the axial position, $\phi$ is the azimuthal angle, and $D_m/2$ is the radial position. The response measured by a generic sensor, which may be realized by receiver 220, over the z axis at a single frequency $\omega$ is denoted by $h_m(z, \phi, D_m/2, \omega)$. FIG. 3A is a representation of a linear measurement system with a delta-like metal loss.

Figure 2B:
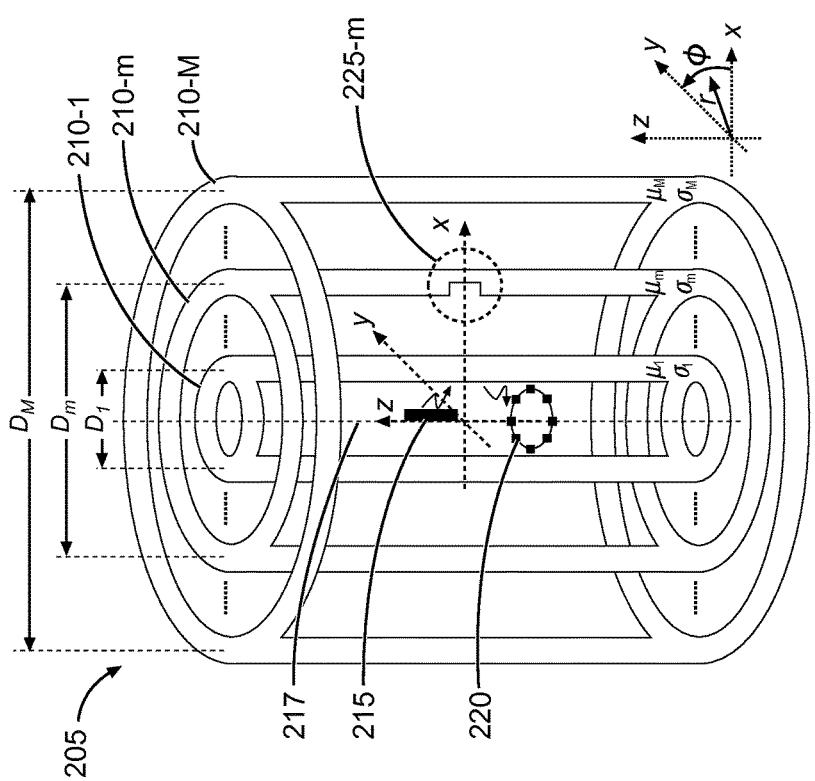
FIG. 2B is a schematic representation of the example linear measurement system with an investigated metal loss region on the $m^{th}$ casing of a multiple-casing structure, in accordance with various embodiments.

FIG. 2B is a schematic representation of the example linear measurement system with an investigated metal loss region 325 on the $m^{th}$ casing of a multiple-casing structure 305, for example, at a well site. The metal loss region 325 may be an arbitrary defect. FIG. 2B shows a transmitter 315 and a receiver 320 along a longitudinal axis 317 in the multi-casing structure 305, similar to FIG. 1. The multi-casing structure 305 may include casings 310-1 . . . 310-m . . . 310-M. Though, FIG. 2B shows three casings (M=3), the multi-casing structure 305 may include more or less than three casings. Casing 310-1 has a diameter, $D_1$, a magnetic permeability, $\mu_1$, and electrical conductivity, $\sigma_1$. Casing 310-m has a diameter $D_m$, a magnetic permeability, $\mu_m$, and electrical conductivity, $\sigma_m$. Casing 310-M has a diameter $D_M$, a magnetic permeability, $\mu_M$, and electrical conductivity, $\sigma_M$. As a non-limiting example, FIG. 2B shows casing 310-m with arbitrary defect 325-m. The transmitter 315 and the receiver 320 can be operated to inspect the casings of the multi-casing structure 305 to determine a response to excitation of casing 310-m and properties of casing 310- m associated with the arbitrary defect 325-m.

Figure 3B:
FIG. 3B is a representation of an investigated metal loss region of the linear measurement system of FIG. 3A, in accordance with various embodiments.

The response $h_m(z, \phi, D_m/2,\omega)$ can be calibrated properly such that it includes the response due to the metal loss only and not due to the tubing/casings. Calibration can be performed by recording the response twice; once with the presence of the metal loss and once without the presence of the metal loss, and then subtracting these two responses. The response without the presence of loss can be obtained from a different section of the sample pipe, another pipe for the same structure and dimensions that does not have a defect, from a database with a response for a material having the same structure and dimensions, a simulation, or combinations thereof. FIG. 3B illustrates the response r due to any arbitrary metal loss function $x(z, \phi, D_m/2)$ in the $m^{th}$ casing as shown in FIG. 2B. The calibrated response r can be written in terms of the delta-like defect response $h_m(z, \phi, D_m/2, \omega)$ and the metal loss function x as:

$$r(z,\phi,D_m/2,\omega) \approx x(z,\phi,D_m/2) **_{2\pi} h_m(z,\phi,D_m/2, \omega) \qquad (1)$$

where * denotes the convolution operation along the z direction and $*_{2\pi}$ denotes $2\pi$-periodic convolution along the $\phi$ direction, since all the functions are periodic along this direction, and $\omega$ denotes the operating frequency.

By taking the Fourier transform (FT) of both sides with respect to the z variable and computing the Fourier series coefficients (FSC) of equation (1) with respect to the $\phi$ variable, one can obtain:

$$R(k_z,n_\phi,D_m/2,\omega) \approx X(k_z,n_\phi,D_m/2) H_m(k_z,n_\phi,D_m/2,\omega) \qquad (2)$$

where R, X, and $H_m$ are obtained from r, x, and h functions, respectively, when taking FT with respect to z variable and computing FSC with respect to the $\phi$ variable, $k_z$ is the Fourier variable corresponding to the z variable, and $n_\phi$ is the index for the FSCs. From equation (2), it is observed that if the calibrated response $h_m$ due to a delta-like flaw in the $m^{th}$ casing is obtained beforehand, and the response due to an arbitrary metal loss function x in the same casing is measured, this metal loss function can be estimated. In order to image the metal loss region using equation (2), a prerequisite step may include a step to estimate the permeability and conductivity of the pipe. This allows for using the previously recorded delta-like defect response in the library corresponding to those electrical property values.

Data acquisition can be conducted at multiple frequencies or in the time-domain. If calibrated responses have been collected at N frequencies for both delta-like and tested flaws, writing equation (2) leads to the following system of equations:

$$\begin{bmatrix} R(k_z, n_\phi, D_m/2, \omega_1) \\ \vdots \\ R(k_z, n_\phi, D_m/2, \omega_N) \end{bmatrix} \approx \begin{bmatrix} H_m(k_z, n_\phi, D_m/2, \omega_1) \\ \vdots \\ H_m(k_z, n_\phi, D_m/2, \omega_N) \end{bmatrix} X(k_z, n_\phi, D_m/2) \qquad (3)$$

This system of equations can be solved for $X(k_z, n_\phi, D_m/2)$. Such separate systems of equations are solved for all $k_z$ and $n_\phi$ values. Once they are solved, the reconstruction of the tested flaw $x(z, n_\phi, D_m/2)$ can be obtained by taking the inverse FT of $X(k_z, n_\phi, D_m/2)$ with respect to the $k_z$ variable and using FSC with respect to the $\phi$ variable.

If time-domain data acquisition has been adopted, such as for pulse eddy current measurements, FT of the collected data can be implemented to obtain frequency-domain data. Then, by proper sampling of the data in the frequency domain, one can construct the system of equations in equation (3). Using multiple frequency data may improve the robustness to noise, significantly.

Consider evaluation of corrosion on multiple casings. So far, discussion has been related to the case where there is corrosion only on one casing. But, this imaging technique can be extended to the case where the corrosion on multiple casings can be evaluated. In such a scenario, the calibrated response can be approximated using the superposition principle. In other words, the calibrated response can be obtained from the sum of the individual responses due to the corrosion on each casing. Thus, assuming imaging of the metal loss variation for casings 1 to M, equation (2) can be written as:

$$R(k_z,n_\phi,\omega) \approx X(k_z,n_\phi,D_1/2) H_1(k_z,n_\phi,D_1/2,\omega) + \ldots + X(k_z,n_\phi,D_M/2) H_M(k_z,n_\phi,D_M/2,\omega) \qquad (4)$$

Writing equation (4) at N frequencies leads to:

$$\overline{R} \approx \overline{H}\overline{X} \tag{5}$$

where $$\overline{R} = \begin{bmatrix} R(k_z, n_\phi, \omega_1) \\ \vdots \\ R(k_z, n_\phi, \omega_N) \end{bmatrix} \tag{6}$$

$$\overline{H} = \begin{bmatrix} H_1(k_z, n_\phi, D_1/2, \omega_1) & \cdots & H_M(k_z, n_\phi, D_M/2, \omega_1) \\ \vdots & \ddots & \vdots \\ H_1(k_z, n_\phi, D_1/2, \omega_N) & & H_M(k_z, n_\phi, D_M/2, \omega_N) \end{bmatrix} \tag{7}$$

$$\overline{X} = \begin{bmatrix} X(k_z, n_\phi, D_1/2) \\ \vdots \\ X(k_z, n_\phi, D_M/2) \end{bmatrix} \tag{8}$$

This system of equations can be solved for $\overline{X}$. Such separate systems of equations are to be solved for all $k_z$ and $n_\phi$ values. Once they are solved, the reconstruction of the images of the casings $x(z, n_\phi, D_m/2)$, $m=1, \ldots, M$ can be obtained by taking the inverse FT of $X(k_z, n_\phi, D_m/2)$, $m=1, \ldots, M$ with respect to the $k_z$ variable and using FSCs with respect to the $\phi$ variable.

Consider separate estimates of defects in a multi-pipe arrangement. FIGS. 4A-4C are schematic representations of receiving responses up to the $1^{st}$, $2^{nd}$, and $3^{rd}$ pipes of a multi-pipe arrangement having at least three pipes by using receivers with variable sizes or numbers of turns of coils. FIG. 4A illustrates receiving the response of the $1^{st}$ pipe only for a tool 470-A along symmetry axis 417-A and having receiver 420-A and transmitter 415-A. FIG. 4B illustrates receiving the responses up to the $2^{nd}$ pipe for a tool 470-B along symmetry axis 417-B and having receiver 420-B and transmitter 415-B. FIG. 4C illustrates receiving the responses up to the $3^{rd}$ pipe for a tool 470-C along symmetry axis 417-C and having receiver 420-C and transmitter 415-C. The dimensions or numbers of turns for the receiver coils 420-A, 420-B, and 420-C can be optimized such that they receive the responses up to the $1^{st}$, $2^{nd}$, or $m^{th}$ pipe only. As shown in FIGS. 4A-4C, the sensed responses can be from farther away from the respective tools as the dimensions or numbers of turns increases from receiver coil 420-A to receiver coil 420-B to receiver coil 420-C. These received signals can be obtained as shown for the same transmitter exciting the respective pipes. Wireline arrangements, or other conventional conveyance techniques, can be used to dispose the tool 470-A, the tool 470-B, and the tool 470-C below the earth's surface at a well site.

Alternatively, transmitters with variable dimensions, variable current levels, or tapped transmitter coils can be employed to excited up to the $1^{st}$ pipe, $2^{nd}$ pipe, or $m^{th}$ pipe, only. FIGS. 5A-5C are schematic representations of excitation of fields with variable strengths to excite up to the $1^{st}$, $2^{nd}$, and $3^{rd}$ pipes by employing a tapped transmitter coil. FIG. 5A illustrates exciting the $1^{st}$ pipe only for a tool 570-A along symmetry axis 517-A and having receiver 520-A and transmitter 515-A. FIG. 5B illustrates exciting up to the $2^{nd}$ pipe for a tool 570-B along symmetry axis 517-B and having receiver 520-B and transmitter 515-B. FIG. 5C illustrates exciting up to the $3^{rd}$ pipe for a tool 570-C along symmetry axis 517-C and having receiver 520-C and transmitter 515 C. As shown in FIGS. 5A-5C, the transmitted field can be propagated farther away from the respective tools as the voltage applied to the respective transmitters is across a large number of numbers of turns or length of transmitter from transmitter coil 515-A to transmitter coil 515-B to transmitter coil 515-C. Wireline arrangements, or other conventional conveyance techniques, can be used to dispose the tool 570-A, the tool 570-B, and the tool 570-C below the earth's surface at a well site. FIGS. 4 and 5 illustrate some of these features for three pipes. This approach may allow for a reduction of the size of the inverse problem and for obtaining some initial estimates for the parameters of the pipes. A similar approach can be applied by using variable frequencies of operation. This can be implemented by employing sufficiently high frequencies to excite the inner most pipes only and avoid receiving responses due to the outer pipes.

Figure 6:
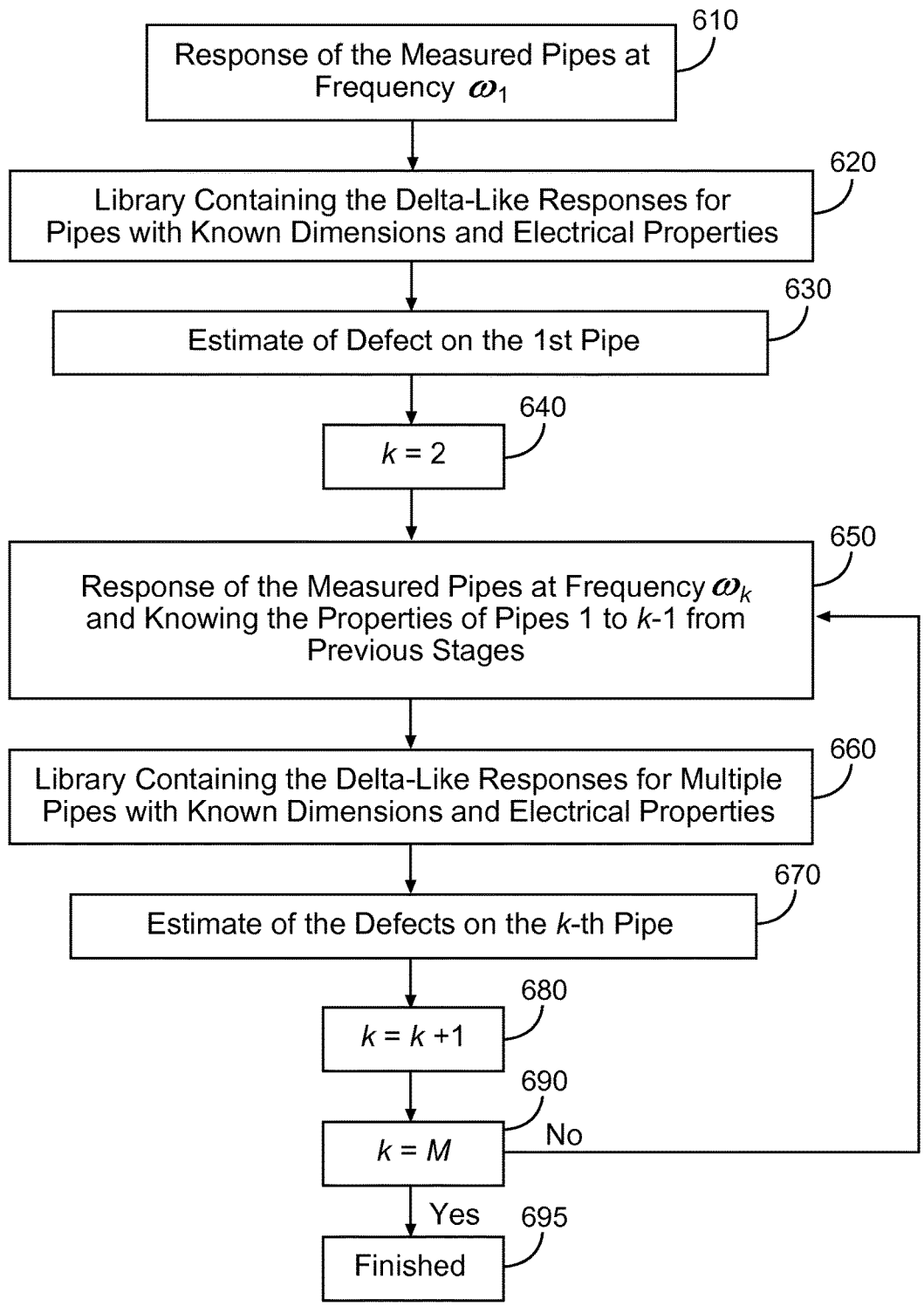
FIG. 6 is a flow diagram of an example iterative algorithm to estimate defects on multiple pipes using frequency domain data, in accordance with various embodiments.

FIG. 6 is a flow diagram of an embodiment of an example iterative algorithm to estimate defects on multiple pipes using frequency domain data. As shown in FIG. 6, the iterative algorithm that can be used to estimate the defects on multiple pipes using multi-frequency data can be implemented assuming that the acquisition frequencies are increasing from $\omega_1$, to $\omega_M$. At 610, the response of the measured pipes at frequency $\omega_1$, is considered. At 620, library containing delta-like defect responses for pipes with known dimensions and electrical properties can be accessed. At 630, estimate of defect on the first pipe can be made. At 640, an index, k, of the pipe under consideration can be set to $k=2$. At 650, response of the measured pipes at frequency $\omega_k$ and knowing the properties and defect functions of pipes 1 to k−1 from previous stages is considered. At 660, a library containing the delta-like defect responses for multiple pipes with known dimensions and electrical properties can be accessed. At 670, estimate of the defects on the kth pipe can be made. At 680, the index of the pipe under consideration can be incremented to k=k+1. At 690, a comparison can be made to determine if the index k has reached the end of the sequence of pipes represented by M. If k does not equal M, the procedure continues at 650 for further processing. If k = M, the procedure can finish at 695.

Consider features of the algorithm of the flow diagram of FIG. 6 with respect to several steps (1 to M) relating R, X, and $H_i$, $i=1, 2, \ldots M$. Step 1 can include solving the following equation when using the response that is influenced by the $1^{st}$ pipe only at frequency $\omega_1$, $$R(k_z, n_\phi, \omega_1) \approx X(k_z, n_\phi, D_1/2) H_1(k_z, n_\phi, D_1/2, \omega_1), \tag{9}$$

to provide an estimate of $X(k_z, n_\phi, D_1/2)$. Step 2 can include solving the following equation when using the response that is influenced up to the $2^{nd}$ pipe at frequency $\omega_2$, and knowing $X(k_z, n_\phi, D_1/2)$ from step 1, $$R(k_z, n_\phi, \omega_2) \approx X(k_z, n_\phi, D_1/2) H_1(k_z, n_\phi, D_1/2, \omega_2) + X(k_z, n_\phi, D_2/2) H_2(k_z, n_\phi, D_2/2, \omega_2) \tag{10}$$

to provide an estimate of $X(k_z, n_\phi, D_2/2)$. This procedure continues in the same manner in which results from the previous step are included in a current step through the last pipe in the multi-pipe arrangement of M pipes. Step M includes solving the following equation when using the response that is influenced up to the $M^{th}$ pipe at frequency $\omega_M$, and knowing $X(k_z, n_\phi, D_1/2)$ to $X(k_z, n_\phi, D_{M-1}/2)$ from steps 1 to M−1, $$R(k_z, n_\phi, \omega_M) \approx X(k_z, n_\phi, D_1/2) H_1(k_z, n_\phi, D_1/2, \omega_M) + \ldots + X(k_z, n_\phi, D_M/2) H_M(k_z, n_\phi, D_M/2, \omega_M) \tag{11}$$

to provide an estimate of $X(k_z, n_\phi, D_M/2)$.

Consider combination of these solutions. A final solution may be computed by combining the responses from the initial estimates and the holographic imaging performed at several frequencies. These frequencies can be the same set of frequencies used for obtaining the initial estimates or they can be selected from a different set of frequencies. To implement the combination, a cost function presented below can be minimized:

$$J=\|\bar{A}(\bar{R}-\bar{\bar{H}}\bar{X})\|+\|\bar{B}(\bar{X}-\bar{\tilde{X}})\| \quad (12)$$

where $\bar{\tilde{X}}$ is the vector containing the initial estimates of defect parameters and $$\bar{\bar{A}} = \begin{bmatrix} a_1 & 0 & \ldots & 0 \\ 0 & a_2 & \ldots & 0 \\ 0 & 0 & \ddots & 0 \\ 0 & 0 & \ldots & a_M \end{bmatrix} \quad (13)$$

$$\bar{\bar{B}} = \begin{bmatrix} b_1 & 0 & \ldots & 0 \\ 0 & b_2 & \ldots & 0 \\ 0 & 0 & \ddots & 0 \\ 0 & 0 & \ldots & b_M \end{bmatrix} \quad (14)$$

Minimization of the second term in the cost function J implies that the final solution should be close to the initial estimate of the defect parameters. The coefficients $a_1$ to $a_M$ can be used to impose weights on how close one wants the estimated parameters to be to the solution obtained from using all frequencies and characterizing all the pipes simultaneously. The coefficients $b_1$ to $b_M$ can be used to impose weights on how close one wants the estimated parameters to be to the initial estimates of the defects. One possibility is to put larger weights for the inner-most pipes and smaller weights for the outer-most pipes. This is due to the fact that the probability of getting more accurate initial estimates for the inner most pipes is higher since their signals are often stronger. Besides, the accuracy of the characterization of the outer-most pipes is influenced by the accuracy of characterization of the inner-most pipes during the initial estimation process that was described earlier. In solving for equation (12), additional constraints may be applied on the X vector based on a-priori knowledge. For example, if a point defect is expected, a non-linear constraint can be used to penalize solutions that are not point like. Mathematically, the cost function can be modified to give large values for non-point like defects through addition of a term. Similarly, if a large defect is expected, solution can be constrained to be large and small defect solution are penalized. Mathematically, the cost function can be modified to give large values for small defects through addition of a term.

In addition, proper coefficients can be applied to the $\bar{\bar{H}}$ matrix to eliminate the components that are masked by noise. For this purpose, the matrix shown in equation (7) can be modified as:

$$\bar{\bar{H}} = \begin{bmatrix} c_{11}H_1(k_z, n_\phi, D_1/2, \omega_1) & \ldots & c_{1M}H_M(k_z, n_\phi, D_M/2, \omega_2) \\ \vdots & \ddots & \vdots \\ c_{M1}H_1(k_z, n_\phi, D_1/2, \omega_M) & \ldots & c_{MM}H_M(k_z, n_\phi, D_M/2, \omega_M) \end{bmatrix} \quad (15)$$

Coefficients $c_{ij}$, i,j=1, ..., M, can be determined based on the level of signal to noise ratio. Proper thresholds can be determined for nominal (non-defected) portions of the pipes. The $c_{ij}$ coefficients for $h_m$ functions (and the corresponding $H_m$ functions) that are below these thresholds can be set to 0 while keeping $c_{ij}$ coefficients for $h_m$ functions (and the corresponding $H_m$ functions) that are above these thresholds as 1. This eliminates their adverse effects on the final solutions. Alternatively, the coefficients $c_{ij}$ can be adjusted properly to reduce the adverse effect of weaker responses acquired from the outer pipes. For example, $c_{ij}$ coefficients can be decreased for any fixed j index, increasing i index to weaken the effect of $H_m$ functions at larger m.

A library can be accessed for delta-like defect responses. In holographic imaging approach as taught herein, calibrated delta-like defect responses can be assumed to be known a priori. This data can be recorded beforehand by measuring delta-like (small) metal loss regions or small holes for various numbers of casings with variable permeability, thickness, and outer diameters. Measuring delta-like metal loss regions or holes may be realized by measuring small metal loss regions or small holes. Alternatively, this information can be obtained from a proper forward model through simulations.

Consider the estimation of the property values for the pipes in a multi-pipe structure. In order to image the metal loss region, a pre-requisite step may include a step to estimate the permeability and conductivity of the pipes, such as casings. This allows for using the previously recorded delta-like defect responses in the library corresponding to those electrical property values.

Figure 7:
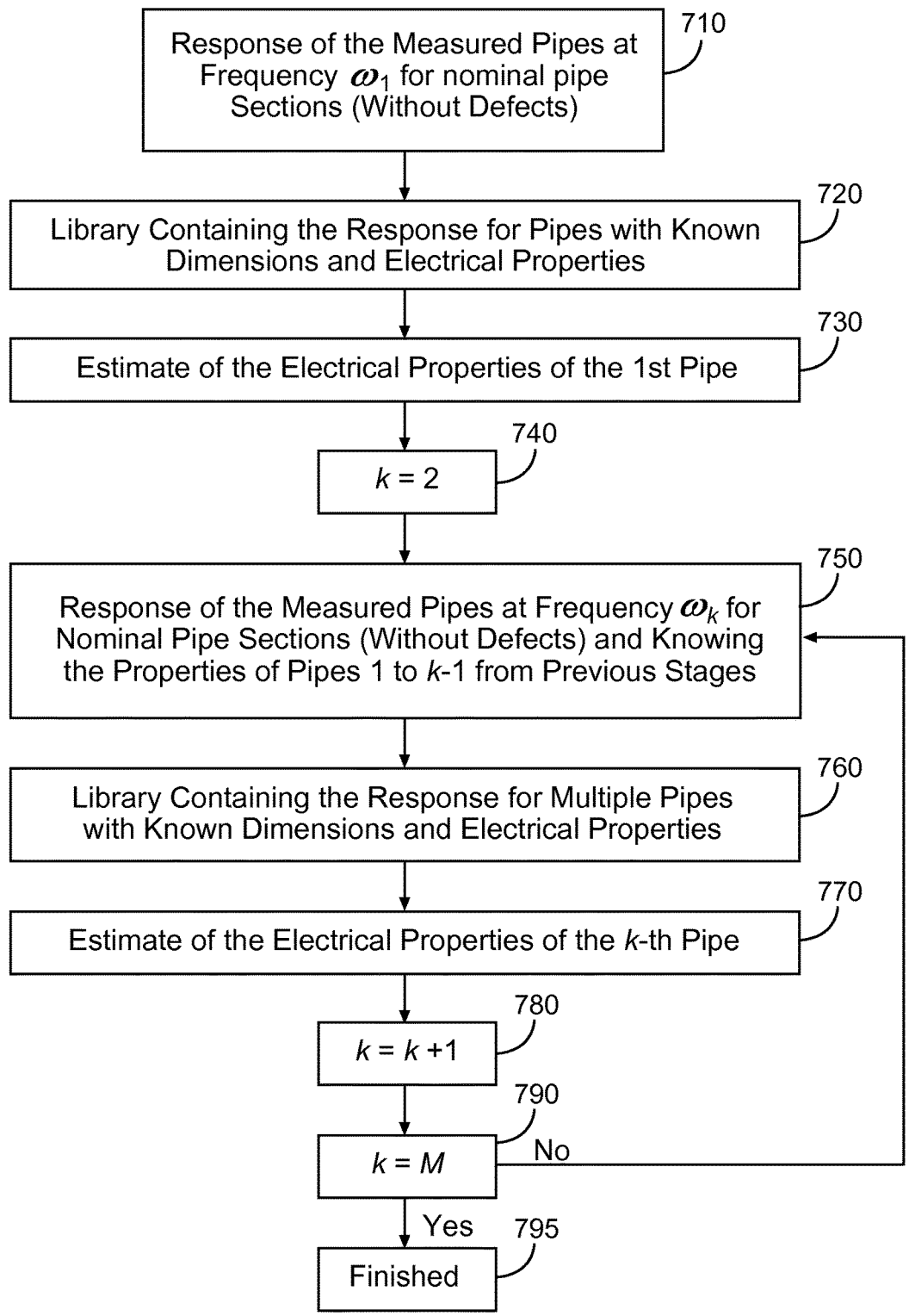
FIG. 7 is a flow diagram of an example iterative algorithm to estimate the electrical properties of multiple pipes using the frequency domain data, in accordance with various embodiments.

When acquiring data at multiple frequencies, the data at higher frequencies can be employed to estimate the electrical property values for inner most pipes first. Then the data at lower frequencies can be employed to estimate the electrical property values for outer most pipes when knowing the electrical properties of the inner pipes from the previous step. The acquired data can be compared with responses in a database for pipes with the same dimensions and known electrical property values to estimate the electrical properties of the measured pipes. FIG. 7 is a flow diagram of an embodiment of an example iterative algorithm to estimate the electrical properties of multiple pipes using the frequency domain data. The acquisition frequencies may be assumed to be increasing from $\omega_1$ to $\omega_M$.

At 710, response of the measured pipes at frequency $\omega_1$ for nominal pipe sections is considered. A nominal pipe section, herein, is a pipe section without defects. At 720, a library containing the response for pipes with known dimensions and electrical properties can be accessed. At 730, an estimate of the electrical properties of the first pipe can be made. At 740, an index, k, of the pipe under consideration can be set to k=2. At 750, response of the measured pipes at frequency $\omega_k$, for nominal pipe sections (without defects) and knowing the properties of pipes 1 to k−1 from previous stages is considered. At 760, a library containing the response for multiple pipes with known dimensions and electrical properties can be accessed. At 770, estimate of the electrical properties of the $k^{th}$ pipe can be made. At 780, the index of the pipe under consideration can be increment to k=k+1. At 790, a comparison can be made to determine if the index k has reached the end of the sequence of pipes represented by M. If k does not equal M, the procedure continues at 750 for further processing. If k=M, the procedure can finish at 795.

While procedures in the flow diagram of FIG. 6 can employ a holographic approach for defect evaluation, the procedures in the flow diagram of FIG. 7 can be based on optimization or pattern matching to estimate the electrical properties. Estimation of the electrical properties performed before estimation of the defects can provide assistance to use proper delta-like defect responses while applying holographic imaging for the defect evaluation.

Figure 8:
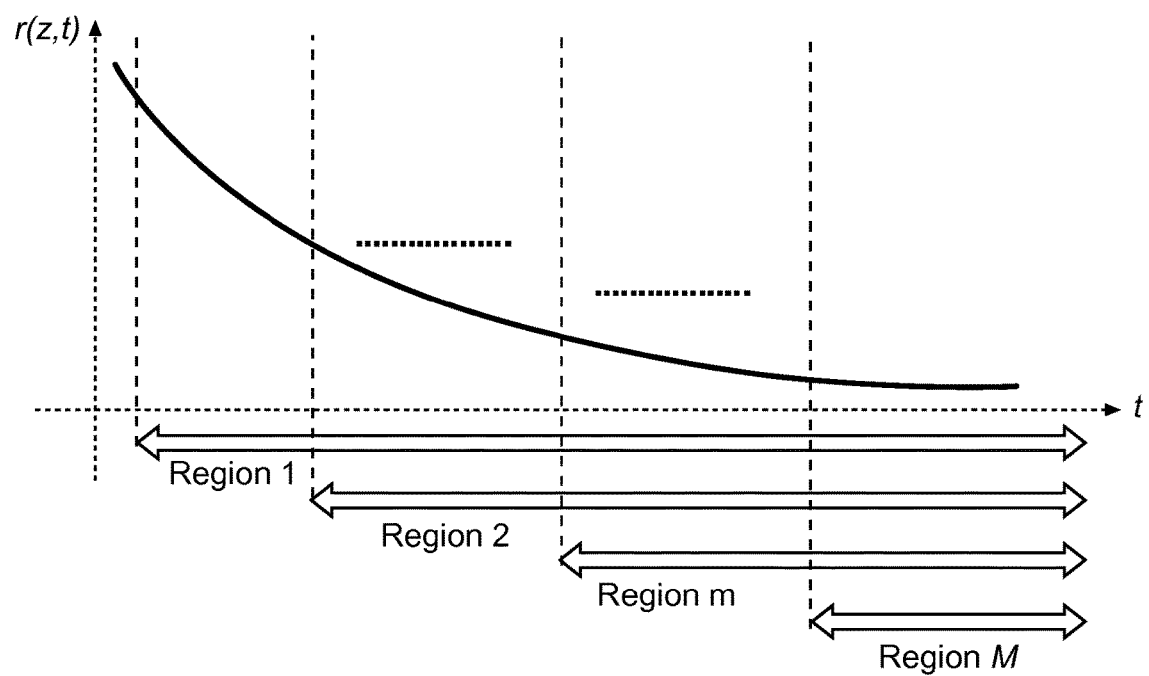
FIG. 8 is a schematic representation of dividing the decay response into M sub-regions, in accordance with various embodiments.

When acquiring data in the time domain, decay responses can be processed. Electrical properties for outer casings begin to affect the response at longer decay times. It is possible to first estimate the properties of the inner most casings from smaller or shorter sensors and then, by having these values, estimate the properties of the outer most casings from the data acquired by larger or longer sensors. It is also possible to estimate the property values of all the casings from the data acquired from the larger or longer sensors. This can be performed by dividing the decay response of the sensor into M regions such that the effect of the $m^{th}$ casing is being observed from the beginning of the $m^{th}$ region. FIG. 8 is a schematic representation of dividing the decay response into M sub-regions. Then, by properly processing the values of the decay response at these sub-regions, the electrical properties of the casings can be estimated.

In an analysis procedure to utilize measured and/or derived data, an inversion process can be implemented. In a logging process such as a real-time logging process, it is not affordable to apply this method for the whole log in one inversion process, because of the numerical cost and the stability issues. However, piece-wise inversion may be implemented. At each depth, a window can be defined centered at that depth and the inversion problem can be solved. A separate depth range can be defined for the solution. After the results at each depth are computed, these results can be combined together to obtain a single and complete 2D image along the depth.

Various of the techniques discussed herein have made use of the Born approximation and delta-like defect response. It is worth mentioning that since this approach is based on the Born approximation, it is valid when the defects are small. Simulations and/or testing may be implemented to determine relative ranges for the smallness of the defects. In addition, due to the same reason, all the results are qualitative and may be employed only for imaging purposes without precisely estimating the thickness value of the casings. The metal loss function x provides an approximate evaluation of the extent of the defect.

Also, the accuracy and resolution of the technique depends on the measurement of the delta-like defect response. The defect for which the delta-like defect response is measured, represents the smallest defect that can be imaged by the system. In other words, it determines the size of each pixel in the image. Any larger defects can then be imaged with similar pixel size.

In the techniques discussed above, the variation of the delta-like defect response with the radial distance over the casing's thickness has been neglected. Alternatively, the delta-like defect response can be measured over the radial distance within the casing and this variation can be included in the image reconstruction process.

The approaches discussed above have application to other type of defects. Although the above discussion is based on thickness changes, the same method may be used to investigate magnetic permeability, conductivity, and diameter changes. In the latter two cases, one has to use the impulse response h and H that corresponds to the particular effect of interest or particular combination of effects of interest. This type of evaluation can be, for example, used in evaluation of stress distributions on the pipe. It can also be used to measure any simultaneous change in pipe diameter and thickness. For example, corrosion on inner or outer side of the pipes can lead to different effective diameter.

It is also possible to obtain multiple image results from different delta function definitions, for example, one based on small thickness change, one based on a hole, one based on a crack, etc., and do a joint visual interpretation from all images. Certain features may be more visible and accurately calculated in one image versus others depending on how the actual feature matches the one used in the definition of the delta.

Figure 9:
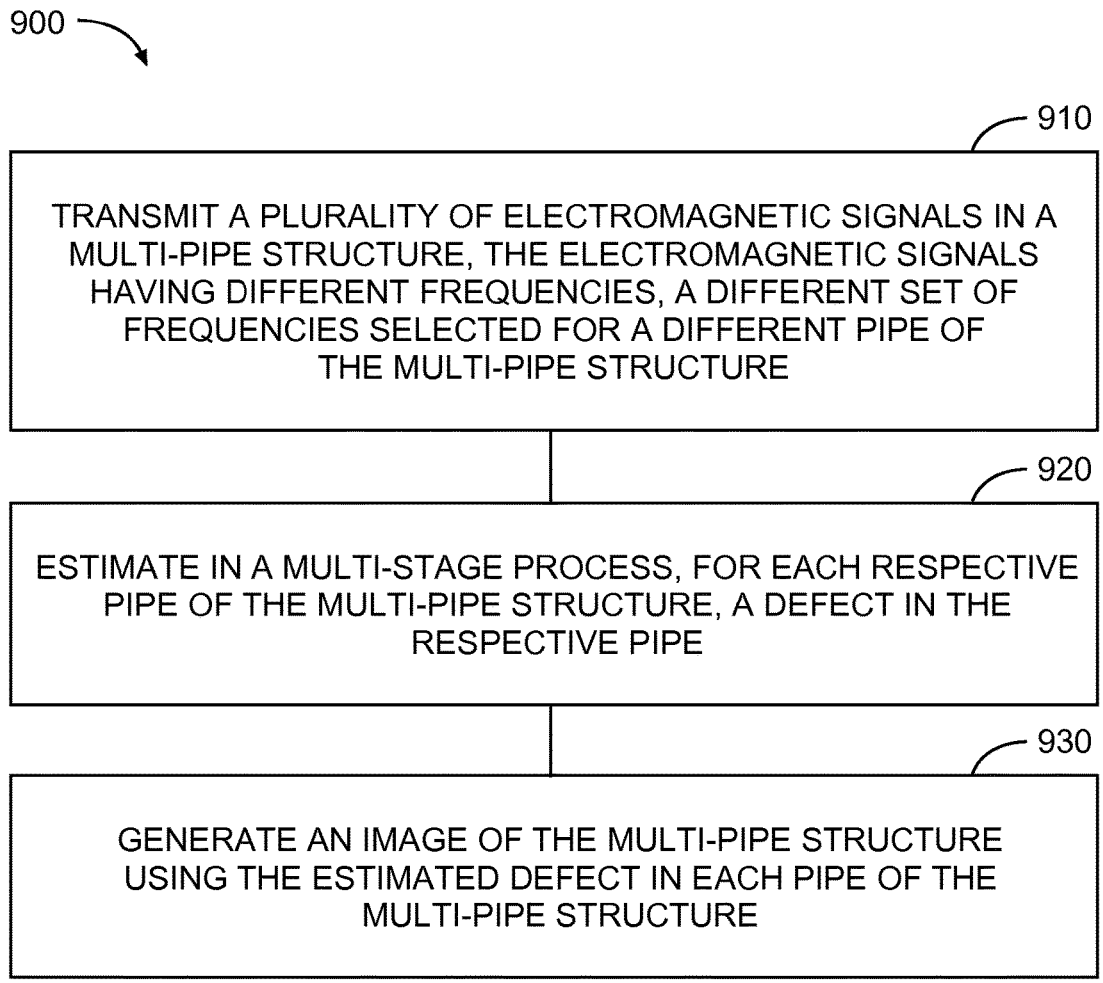
FIG. 9 is a flow diagram of an example method of generating an image of a multi-pipe structure including defects in the pipes of the multi-pipe structure, in accordance with various embodiments.

FIG. 9 is a flow diagram of an embodiment of an example method 900 of generating an image of a multi-pipe structure including defects in the pipes of the multi-pipe structure. At 910, a plurality of electromagnetic signals is transmitted in a multi-pipe structure, the electromagnetic signals having different frequencies, a different set of frequencies selected for a different pipe (or set of pipes) of the multi-pipe structure. At 920, for each respective pipe (or set of pipes) of the multi-pipe structure, the defect in the respective pipe (or set of pipes) is estimated in a multi-stage process, under control of a processor. A procedure of estimating the defect in the respective pipe (or set of pipes) can include using a delta-like defect response for each pipe of the multi-pipe structure that is excited at the selected frequency (or set of frequencies) of the respective pipe (or set of pipes); using an estimated defect of each pipe, other than the respective pipe (or set of pipes), that is excited by the selected frequency (or set of frequencies) of the respective pipe (or set of pipes); and using a received response from transmitting the electromagnetic signal at the selected frequency (or set of frequencies) of the respective pipe (or set of pipes). At 930, an image of the multi-pipe structure is generated using the estimated defect in each pipe of the multi-pipe structure.

In methods identical or similar to method 900, estimating, for each respective set of pipes of the multi-pipe structure, the defect in the respective pipes can include estimating the defect for each respective set of pipes of the multi-pipe structure in ordered stages beginning with the innermost set of pipes and ending with the outermost set of pipes in an order based on a diameter of the pipes of the multi-pipe structure and with each electromagnetic signal at its selected set of frequencies exciting only the pipe assigned to the selected set of frequencies and pipes having a smaller diameter than the set of pipes assigned to the selected set of frequencies. In such methods, the selected set of frequencies decrease in magnitude in order from the selected set of frequencies assigned to the innermost pipes to the selected set of frequencies assigned to the outermost pipes. In such methods or similar methods, processing a first stage of the ordered stages to estimate the defect in the innermost pipes can include acquiring a response from the innermost pipes excited at the selected frequencies and applying an a priori calibrated delta-like defect responses for the pipes with known dimensions and electrical properties substantially equal to the innermost pipes; and processing subsequent stages such that each stage k, k being an integer from 2 to the number of pipes of the multiple-pipe structure, includes estimating defects on the $k^{th}$ pipe (or $k^{th}$ set of pipes) by acquiring responses of the pipes at the selected frequency (set of frequencies) of the $k^{th}$ pipe (or $k^{th}$ set of pipes) and applying known properties of pipes 1 to k−1 (or set of pipes 1 to k−1) of the multiple-pipe structure from previous stages along with a priori calibrated delta-like defect responses with known dimensions and electrical properties for pipes 1 to k−1 (or set of pipes 1 to k−1) at the selected frequency (or set of frequencies) of the $k^{th}$ pipe (or $k^{th}$ set of pipes).

In methods identical or similar to method 900, prior to estimating, for each respective pipe of the multi-pipe structure, a defect in the respective pipe, such methods can include estimating permeability and conductivity of the pipes of the multi-pipe structure. Such methods or similar methods can include acquiring data at multiple frequencies for non-defect sections of the pipes of the multi-pipe structure, the data at higher frequencies employed to estimate the electrical property values for inner most pipes first; employing data at lower frequencies for non-defect sections of the pipes of the multi-pipe structure to estimate the electrical property values for outer most pipes using electrical properties of the inner pipes from employing the data at higher frequencies; and comparing data for each pipe, after processing with respect to other pipes of the multi-pipe structure, with responses in a database with known electrical property values for pipes having the same dimensions to estimate the electrical properties of the pipes of the multi-pipe structure. Such methods or similar methods can include acquiring data in the time domain from exciting the pipes of the multi-pipe structure, the data including a decay response of a sensor; dividing the decay response of the sensor into M sub-regions such that the effect of the $m^{th}$ pipe is being observed from the beginning of the $m^{th}$ sub-region; and processing values of the decay response at these sub-regions to estimate electrical properties of the pipes.

In methods identical or similar to method 900 and methods discussed above, such methods can include receiving responses from selected ones of the pipes of the multi-pipe structures by using receivers with variable sizes or numbers of turns, or by using transmitters with variable dimensions, variable current levels, or tapped transmitter coils to excite the selected ones of the pipes. In various embodiments, a non-transitory machine-readable storage device can comprise instructions stored thereon, which, when performed by a machine, cause the machine to perform operations, the operations comprising one or more features similar to or identical to features of methods and techniques described with respect to method 900, variations thereof, and/or features of other methods taught herein such as associated with FIGS. 6 and 7. The physical structures of such instructions may be operated on by one or more processors. Executing these physical structures can cause the machine to perform operations comprising transmitting a plurality of electromagnetic signals in a multi-pipe structure, the electromagnetic signals having different frequencies, each different frequency (or set of frequencies) selected for a different pipe (or set of pipes) of the multi-pipe structure; estimating, for each respective pipe (or set of pipes) of the multi-pipe structure, a defect in the respective pipe (or set of pipes) by: using a delta-like defect response for each pipe (or set of pipes) of the multi-pipe structure that is excited at the selected frequency (or set of frequencies) of the respective pipe (or set of pipes); using an estimated defect of each pipe (or set of pipes), other than the respective pipe (or set of pipes), that is excited by the selected frequency (or set of frequencies) of the respective pipe (or set of pies); and using a received response from transmitting the electromagnetic signal at the selected frequency (or set of frequencies) of the respective pipe (or set of pipes); and generating an image of the multi-pipe structure using the estimated defect in each pipe of the multi-pipe structure. The instructions can include instructions to operate a tool or tools having sensors disposed in a multi-pipe structure downhole in a borehole to provide data to process in accordance with the teachings herein. The multi-pipe structure may be realized as a multi-casing structure disposed in a borehole at a well site.

Further, a machine-readable storage device, herein, is a physical device that stores data represented by physical structure within the device. Such a physical device is a non-transitory device. Examples of machine-readable storage devices can include, but are not limited to, read only memory (ROM), random access memory (RAM), a magnetic disk storage device, an optical storage device, a flash memory, and other electronic, magnetic, and/or optical memory devices.

Figure 10:
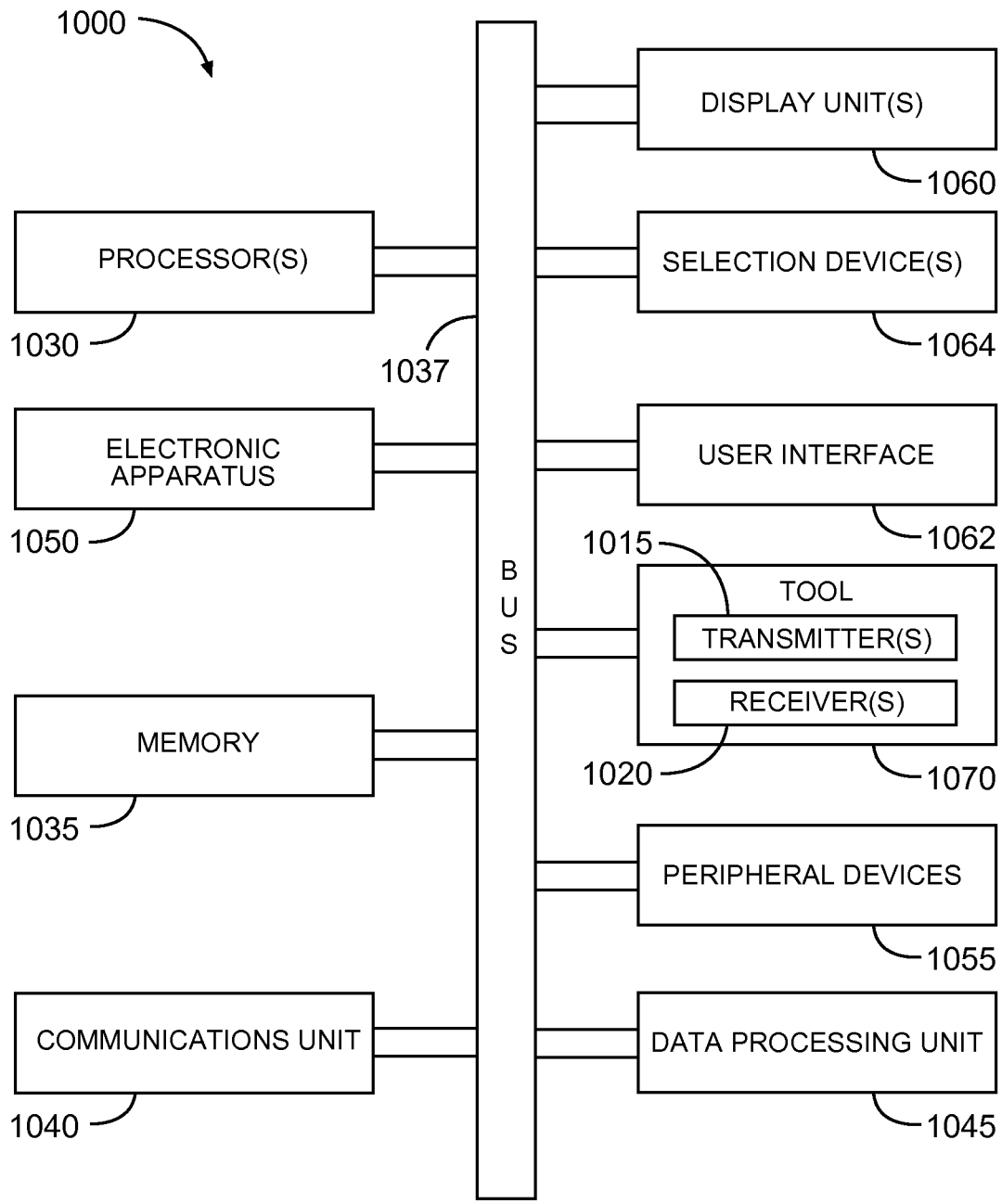
FIG. 10 is a block diagram of features of an example system operable to execute schemes associated with two-dimensional imaging with multi-stage processing, in accordance with various embodiments.

FIG. 10 is a block diagram of features of an embodiment of an example system 1000 operable to execute schemes associated with two-dimensional imaging with multi-stage processing of a multi-pipe structure. The system 1000 can be implemented at a well site to, among other things, image a multi-pipe structure disposed in a borehole. The multi-pipe structure may be a production structure of the well site.

The system 1000 can comprise a set of transmitters 1015, a set of receivers 1020, and a processor 1030. The transmitters 1015 can be arrangeable in the multi-pipe structure to transmit a plurality of electromagnetic signals in the multi-pipe structure and the set of receivers 1020 can be arrangeable in the multi-pipe structure to receive signals in response to exciting pipes in the multi-pipe structure. The set of receivers 1020 and/or the set of transmitters 1015 can be structured such that received responses are operatively received only from a selected pipe (or set of pipes) of the multi-pipe structure and from pipes (or set of pipes) interior to the selected pipe (or set of pipes) in the multi-pipe structure. The set of receivers 1020 can include receivers with variable sizes or numbers of turns of coils. The set of transmitters 1015 can include transmitters with variable dimensions or tapped transmitter coils to excite the selected ones of the pipes. The processor 1030 can be arranged to control variable current levels to the set of transmitters to excite the selected ones of the pipes. The set of receivers 1020 and/or the set of transmitters 1015 can be arranged in a manner similar to or identical to arrangements as taught with respect to FIGS. 1-9. The set of receivers 1020 may be realized by one or more receivers and the set of transmitters 1015 may be realized by one or more transmitters. System 1000 can be implemented to operate in a manner as taught herein to image the multi-pipe structure such as but not limited to the teaching associated with FIGS. 1-9.

The processor 1030 can be arranged to estimate, for each respective pipe of the multi-pipe structure investigated by a tool 1070 containing the set of receivers 1020 and/or the set of transmitters 1015, a defect in the respective pipe. The processor 1030 can be arranged to: use delta-like defect responses for each pipe (or set of pipes) of the multi-pipe structure that is excited at a selected frequency (or set of frequencies) of the respective pipe (or set of pipes); use an estimated defect of each pipe (or set of pipes), other than the respective pipe (or set of pipes), that is excited by the selected frequency (or set of frequencies) of the respective pipe (or set of pipes); and use a received response from transmission of the electromagnetic signal at the selected frequency (or set of frequencies) of the respective pipe (or set of pipes). The processor 1030 can be arranged to generate an image of the multi-pipe structure by use of the estimated defect in each pipe (or set of pipes) of the multi-pipe structure. The processor 1030 can control the display of the image on one or more display units 1060. The processor 1030 can be realized by one or more processors 1030.

The processor 1030 can be arranged to estimate the defect for each respective pipe (or set of pipes) of the multi-pipe structure in ordered stages beginning with the innermost pipes and ending with the outermost pipes in an order based on a diameter of the pipes of the multi-pipe structure and with each electromagnetic signal at a selected frequency (or set of frequencies) exciting only the pipe (or set of pipes) assigned to the selected frequency (or set of frequencies) and pipes having a smaller diameter than the pipe (or set of pipes) assigned to the selected frequency (or set of frequencies). The selected frequencies can be larger in magnitude in order from the selected frequencies assigned to the innermost pipes to the selected frequencies assigned to the outermost pipes. The processor 1030 can be arranged to process a first stage of the ordered stages to estimate the defect in the innermost pipes with the processor arranged to acquire a response from the innermost pipes excited at the selected frequencies and apply an a priori calibrated delta-like defect responses for the pipes with known electrical properties having dimensions substantially equal to the innermost pipes. The processor 1030 can be arranged to process subsequent stages such that for each stage k, k being an integer from 2 to the number of pipes (or number of set of pipes) of the multiple-pipe structure, the processor 1030 can be arranged to estimate defects on the $k^{th}$ pipe (or $k^{th}$ set of pipes) by acquisition of responses of the pipes at the selected frequency (or set of frequencies) of the $k^{th}$ pipe (or $k^{th}$ set of pipes) and application of known properties of pipes (or set of pipes) 1 to k−1 of the multiple-pipe structure from previous stages along with a priori calibrated delta-like defect response with known dimensions and electrical properties for pipes (or set of pipes) 1 to k−1 at the selected frequency (or set of frequencies) of the $k^{th}$ pipe (or $k^{th}$ set of pipes).

The processor 1030 can be arranged to estimate permeability and conductivity of the pipes of the multi-pipe structure, prior to the estimate, for each respective pipe of the multi-pipe structure, of a defect in the respective pipe. The processor 1030 can be arranged to: acquire data at multiple frequencies for non-defect sections of the pipes of the multi-pipe structure, the data at higher frequencies utilized to estimate the electrical property values for inner most pipes first; employ data at lower frequencies for non-defect sections of the pipes of the multi-pipe structure to estimate the electrical property values for outer most pipes by use of electrical properties of the inner pipes from utilization of the data at higher frequencies; and compare data for each pipe, after processing with respect to other pipes of the multi-pipe structure, with responses in a database with known electrical property values for pipes having the same dimensions to estimate the electrical properties of the pipes of the multi-pipe structure. The processor 1030 can be arranged to acquire data in the time domain from excitation of the pipes of the multi-pipe structure, the data including a decay response of a sensor; divide the decay response of the sensor into M sub-regions such that the effect of the $m^{th}$ pipe is being observed from the beginning of the $m^{th}$ sub-region; and process values of the decay response at these sub-regions to estimate electrical properties of the pipes.

Though the processor 1030 can control operation of the components of system 1000 to estimate permeability and conductivity of the pipes of the multi-pipe structure prior to operating to image the multi-pipe structure, the processor 1030 can direct access of the estimates permeability and conductivity from a database. The database can include such parameters for pipes having known material structures and pipe designs without defects.

The system 1000 can include a user interface 1062 operable with the processors 1030, a data processing unit 1045 operable with the user interface 1062, where the processors 1030, the user interface 1062, and the data processing unit 1045 are structured to be operated according to any scheme similar to or identical to the schemes associated with imaging a multi-pipe structure as taught herein. In an embodiment, processor(s) 1030 can be realized as a single processor or a group of processors. Processors of the group of processors may operate independently depending on an assigned function. The system 1000 can be arranged to perform various operations on the data, acquired from the tool 1070 operational in a multi-pipe structure, in a manner similar or identical to any of the processing techniques discussed herein.

The system 1000 can be arranged as a distributed system. Data from operating the tool 1070 at various depths in the multi-pipe structure can be processed by the one or more processors 1030. Alternatively, imaging may be conducted by the data processing unit 1045 as a dedicated imaging module.

The system 1000 can include a memory 1035, an electronic apparatus 1050, and a communications unit 1040. The processor(s) 1030, the memory 1035, and the communications unit 1040 can be arranged to operate as a processing unit to control management of tool 1070 and to perform operations on data signals collected by the tool 1070. The memory 1035 can include a database having information and other data such that the system 1000 can operate on data from the tool 1070. In an embodiment, the data processing unit 1045 can be distributed among the components of the system 1000 including memory 1035 and/or the electronic apparatus 1050.

The communications unit 1040 can include downhole communications for communication to the surface at a well site from the tool 1070 in a multi-pipe structure. The communications unit 1040 may use combinations of wired communication technologies and wireless technologies at frequencies that do not interfere with on-going measurements. The communications unit 1040 can allow for a portion or all of the data analysis to be conducted within a multi-pipe structure with results provided to the user interface 1062 for presentation on the one or more display unit(s) 1060 aboveground. The communications unit 1040 can provide for data to be sent aboveground such that substantially all analysis is performed aboveground. The data collected by the tool 1070 can be stored with the tool 1070 that can be brought to the surface to provide the data to the one or more processors 1030, the user interface 1062, and the data processing unit 1045. The communications unit 1040 can allow for transmission of commands to tool 1070 in response to signals provided by a user through the user interface 1062.

The system 1000 can also include a bus 1037, where the bus 1037 provides electrical conductivity among the components of the system 1000. The bus 1037 can include an address bus, a data bus, and a control bus, each independently configured. The bus 1037 can be realized using a number of different communication mediums that allows for the distribution of components of the system 1000. Use of the bus 1037 can be regulated by the processor(s) 1030. The bus 1037 can include a communications network to transmit and receive signals including data signals and command and control signals.

In various embodiments, the peripheral devices 1055 can include drivers to provide voltage and/or current input to the set of transmitters 1015, additional storage memory and/or other control devices that may operate in conjunction with the processor(s) 1030 and/or the memory 1035. The display unit(s) 1060 can be arranged with a screen display, as a distributed component on the surface, that can be used with instructions stored in the memory 1035 to implement the user interface 1062 to manage the operation of the tool 1070 and/or components distributed within the system 1000. Such a user interface can be operated in conjunction with the communications unit 1040 and the bus 1037. The display unit(s) 1060 can include a video screen, a printing device, or other structure to visually project data/information and images. The system 1000 can include a number of selection devices 1064 operable with the user interface 1062 to provide user inputs to operate the data processing unit 1045 or its equivalent. The selection device(s) 1064 can include one or more of a touch screen or a computer mouse operable with the user interface 1062 to provide user inputs to operate the data processing unit 1045.

A method 1 can comprise: transmitting a plurality of electromagnetic signals in a multi-pipe structure, the electromagnetic signals having different frequencies, a different set of frequencies selected for a different pipe of the multi-pipe structure; estimating, under control of a processor, for each respective pipe of the multi-pipe structure, a defect in the respective pipe by: using a delta-like response for each pipe of the multi-pipe structure that is excited at the selected set of frequencies of the respective pipe; using an estimated defect of each pipe, other than the respective pipe, that is excited by the selected set of frequencies of the respective pipe; and using a received response from transmitting the electromagnetic signal at the selected set of frequencies of the respective pipe; and generating an image of the multi-pipe structure using the estimated defect in each pipe of the multi-pipe structure.

A method 2 can include elements of method 1 and can include the different frequencies selected from a range between 0.1 Hz and 1000 Hz and at least one of the frequencies used is sensitive mostly to the first pipe.

A method 3 can include elements of any of methods 1 and 2 and can include estimating the defect in a pipe of the multi-pipe structure being derived by solving a linear system of equations that contains the delta-like responses of each pipe of the multi-pipe structure, and the received responses measured in at least one receiver to the plurality of electromagnetic signals generated having at least two frequencies by at least one transmitter.

A method 4 can include elements of any of methods 1-3 and can include solving the linear system of equations to include solving by a least square method.

A method 5 can include elements of any of methods 1-4 and can include estimating, for each respective pipe of the multi-pipe structure, the defect in the respective pipe to include estimating the defect for each respective pipe of the multi-pipe structure in ordered stages beginning with the innermost pipe and ending with the outermost pipe in an order based on a diameter of the pipes of the multi-pipe structure and with each electromagnetic signal at its selected set of frequencies exciting only the pipe assigned to the selected set of frequencies and pipes having a smaller diameter than the pipe assigned to the selected set of frequencies.

A method 6 can include elements of any of methods 1-5 and can include averages of the selected sets of frequencies decrease in magnitude in order from an average of the selected set of frequencies assigned to the innermost pipe to an average of the selected set of frequencies assigned to the outermost pipe.

A method 7 can include elements of any of methods 1-6 and can include processing a first stage of the ordered stages to estimate the defect in the innermost pipe to include acquiring a response from the innermost pipe excited at the selected set of frequencies and applying an a priori calibrated delta-like response for a pipe with known dimensions and electrical properties substantially equal to the innermost pipe; and processing subsequent stages such that each stage k, k being an integer from 2 to the number of pipes of the multiple-pipe structure, includes estimating defects on the $k^{th}$ pipe by acquiring responses of the pipes at the selected set of frequencies of the $k^{th}$ pipe and applying known properties of pipes 1 to k−1 of the multiple-pipe structure from previous stages along with a priori calibrated delta-like response with known dimensions and electrical properties for pipes 1 to k−1 at the selected set of frequencies of the $k^{th}$ pipe.

A method 8 can include elements of any of methods 1-7 and can include prior to estimating, for each respective pipe of the multi-pipe structure, a defect in the respective pipe, estimating permeability and conductivity of the pipes of the multi-pipe structure.

A method 9 can include elements of any of methods 1-8 and can include estimating the conductivity and permeability of the pipes to comprise selecting a response from a precomputed library of calibrated responses.

A method 10 can include elements of any of methods 1-9 and can include estimating the conductivity and permeability of the pipes comprises performing an inversion on a non-defected section with nominal thickness of the multi-pipe structure.

A method 11 can include elements of any of methods 1-10 and can include: acquiring data at multiple frequencies for non-defect sections of the pipes of the multi-pipe structure, the data at higher frequencies employed to estimate the electrical property values for inner most pipes first; employing data at lower frequencies for non-defect sections of the pipes of the multi-pipe structure to estimate the electrical property values for outer most pipes using electrical properties of the inner pipes from employing the data at higher frequencies; and comparing data for each pipe, after processing with respect to other pipes of the multi-pipe structure, with responses in a database with known electrical property values for pipes having the same dimensions to estimate the electrical properties of the pipes of the multi-pipe structure.

A method 12 can include elements of any of methods 1-11 and can include: acquiring data in the time domain from exciting the pipes of the multi-pipe structure, the data including a decay response of a sensor; dividing the decay response of the sensor into M sub-regions such that the effect of the $m^{th}$ pipe is being observed from the beginning of the $m^{th}$ sub-region; and processing values of the decay response at these sub-regions to estimate electrical properties of the pipes.

A method 13 can include elements of any of methods 1-12 and can include receiving responses from selected ones of the pipes of the multi-pipe structures by using receivers with variable sizes or numbers of turns, or by using transmitters with variable dimensions, variable current levels, or tapped transmitter coils to excite the selected ones of the pipes.

A machine-readable storage device 1 having instructions stored thereon, which, when executed by one or more processors of a machine, cause the machine to perform operations, the operations comprising: transmitting a plurality of electromagnetic signals in a multi-pipe structure, the electromagnetic signals having different frequencies, a different set of frequencies selected for a different pipe of the multi-pipe structure; estimating, for each respective pipe of the multi-pipe structure, a defect in the respective pipe by: using a delta-like response for each pipe of the multi-pipe structure that is excited at the selected set of frequencies of the respective pipe; using an estimated defect of each pipe, other than the respective pipe, that is excited by the selected set of frequencies of the respective pipe; and using a received response from transmitting the electromagnetic signal at the selected set of frequencies of the respective pipe; and generating an image of the multi-pipe structure using the estimated defect in each pipe of the multi-pipe structure.

A machine-readable storage device 2 can include elements of machine-readable storage device 1 and can include estimating, for each respective pipe of the multi-pipe structure, the defect in the respective pipe includes estimating the defect for each respective pipe of the multi-pipe structure in ordered stages beginning with the innermost pipe and ending with the outermost pipe in an order based on a diameter of the pipes of the multi-pipe structure and with each electromagnetic signal at its selected set of frequencies exciting only the pipe assigned to the selected set of frequencies and pipes having a smaller diameter than the pipe assigned to the selected set of frequencies.

A machine-readable storage device 3 can include elements of any of machine-readable storage devices 1 and 2 and can include averages of the selected sets of frequencies decreasing in magnitude in order from an average of the selected set of frequencies assigned to the innermost pipe to an average of the selected sets of frequencies assigned to the outermost pipe.

A machine-readable storage device 4 can include elements of any of machine-readable storage devices 1-3 and can include processing a first stage of the ordered stages to estimate the defect in the innermost pipe to include acquiring a response from the innermost pipe excited at the selected set of frequencies and applying an a priori calibrated delta-like response for a pipe with known dimensions and electrical properties substantially equal to the innermost pipe; and processing subsequent stages such that each stage k, k being an integer from 2 to the number of pipes of the multiple-pipe structure, includes estimating defects on the $k^{th}$ pipe by acquiring responses of the pipes at the selected set of frequencies of the $k^{th}$ pipe and applying known properties of pipes 1 to k–1 of the multiple-pipe structure from previous stages along with a priori calibrated delta-like response with known dimensions and electrical properties for pipes 1 to k–1 at the selected set of frequencies of the $k^{th}$ pipe.

A machine-readable storage device 5 can include elements of any of machine-readable storage devices 1-4 and can include prior to estimating, for each respective pipe of the multi-pipe structure, a defect in the respective pipe, the operations to include estimating permeability and conductivity of the pipes of the multi-pipe structure.

A machine-readable storage device 6 can include elements of any of machine-readable storage devices 1-5 and can include operations to include: acquiring data at multiple frequencies for non-defect sections of the pipes of the multi-pipe structure, the data at higher frequencies employed to estimate the electrical property values for inner most pipes first; employing data at lower frequencies for non-defect sections of the pipes of the multi-pipe structure to estimate the electrical property values for outer most pipes using electrical properties of the inner pipes from employing the data at higher frequencies; and comparing data for each pipe, after processing with respect to other pipes of the multi-pipe structure, with responses in a database with known electrical property values for pipes having the same dimensions to estimate the electrical properties of the pipes of the multi-pipe structure.

A machine-readable storage device 7 can include elements of any of machine-readable storage devices 1-6 and can include operations to include: acquiring data in the time domain from exciting the pipes of the multi-pipe structure, the data including a decay response of a sensor; dividing the decay response of the sensor into M sub-regions such that the effect of the $m^{th}$ pipe is being observed from the beginning of the $m^{th}$ sub-region; and processing values of the decay response at these sub-regions to estimate electrical properties of the pipes.

A system 1 can comprise: a set of transmitters arrangeable in a multi-pipe structure to transmit a plurality of electromagnetic signals in the multi-pipe structure; a set of receivers arrangeable in the multi-pipe structure to receive signals in response to exciting pipes in the multi-pipe structure, the set of receivers and/or the set of transmitters structured such that received responses are operatively received only from a selected pipe of the from multi-pipe structure and from pipes interior to the selected pipe in the multi-pipe structure; a processor arranged to estimate, for each respective pipe of the multi-pipe structure, a defect in the respective pipe by: use of a delta-like response for each pipe of the multi-pipe structure that is excited at a selected set of frequencies of the respective pipe; use of an estimated defect of each pipe, other than the respective pipe, that is excited by the selected set of frequencies of the respective pipe; and use of a received response from transmission of the electromagnetic signal at the selected set of frequencies of the respective pipe; and arranged to generate an image of the multi-pipe structure by use of the estimated defect in each pipe of the multi-pipe structure.

A system 2 can include elements of system 1 and can include the processor arranged to estimate, for each respective pipe of the multi-pipe structure, the defect in the respective pipe includes the processor arranged to estimate the defect for each respective pipe of the multi-pipe structure in ordered stages beginning with the innermost pipe and ending with the outermost pipe in an order based on a diameter of the pipes of the multi-pipe structure and with each electromagnetic signal at a selected set of frequencies exciting only the pipe assigned to the selected set of frequencies and pipes having a smaller diameter than the pipe assigned to the selected set of frequencies.

A system 3 can include elements of any of systems 1 and 2 and can include averages of the selected sets of frequencies being larger in magnitude in order from an average of the selected set of frequencies assigned to the innermost pipe to an average of the selected set of frequencies assigned to the outermost pipe.

A system 4 can include elements of any of systems 1-3 and can include the processor arranged to process a first stage of the ordered stages to estimate the defect in the innermost pipe with the processor arranged to acquire a response from the innermost pipe excited at the selected set of frequencies and apply an a priori calibrated delta-like response for a pipe with known electrical properties having dimensions substantially equal to the innermost pipe; and to process subsequent stages such that each stage k, k being an integer from 2 to the number of pipes of the multiple-pipe structure, the processor is arranged to estimate defects on the k-th pipe by acquisition of responses of the pipes at the selected set of frequencies of the kth pipe and application of known properties of pipes 1 to k–1 of the multiple-pipe structure from previous stages along with a priori calibrated delta-like response with known dimensions and electrical properties for pipes 1 to k–1 at the selected frequency of the kth pipe.

A system 5 can include elements of any of systems 1-4 and can include the processor arranged to estimate permeability and conductivity of the pipes of the multi-pipe structure, prior to the estimate, for each respective pipe of the multi-pipe structure, of a defect in the respective pipe.

A system 6 can include elements of any of systems 1-5 and can include the processor arranged to: acquire data at multiple frequencies for non-defect sections of the pipes of the multi-pipe structure, the data at higher frequencies utilized to estimate the electrical property values for inner most pipes first; employ data at lower frequencies for non-defect sections of the pipes of the multi-pipe structure to estimate the electrical property values for outer most pipes by use of electrical properties of the inner pipes from utilization of the data at higher frequencies; and compare data for each pipe, after processing with respect to other pipes of the multi-pipe structure, with responses in a database with known electrical property values for pipes having the same dimensions to estimate the electrical properties of the pipes of the multi-pipe structure.

A system 7 can include elements of any of systems 1-6 and can include the processor arranged to: acquire data in the time domain from excitation of the pipes of the multi-pipe structure, the data including a decay response of a sensor; divide the decay response of the sensor into M sub-regions such that the effect of the $m^{th}$ pipe is being observed from the beginning of the $m^{th}$ sub-region; and process values of the decay response at these sub-regions to estimate electrical properties of the pipes.

A system 8 can include elements of any of systems 1-7 and can include the set of receivers to include receivers with variable sizes or numbers of turns.

A system 9 can include elements of any of systems 1-8 and can include the set of transmitters to include transmitters with variable dimensions or tapped transmitter coils to excite the selected ones of the pipes.

A system 10 can include elements of any of systems 1-9 and can include the processor arranged to control variable current levels to the set of transmitters to excite the selected ones of the pipes.

Systems and methods, as taught herein, can utilize data acquisition at multiple frequencies to reconstruct 2D images of casings. Proper number and configuration of sensors as well as acquisition frequencies provide a means to qualitatively image the casings using the measurements along the axial direction. Proper number and configuration of sensors may be provided from testing, accumulated data from previous measurements, simulations, and combinations thereof. The capabilities of resolving defects on separate casings and also imaging the defects on each casing, with better resolution, paves the way toward proper remedial actions for the casings.

Analysis of casing condition is an important procedure, as tubing/casing removal is both expensive and time consuming, particularly in offshore platforms. This new approach provides high resolution imaging of the casing. With proper EM transmitters and receivers and proper library, imaging can be performed for multiple casings and for casings with larger OD. This can allow for better interpretation of the integrity of the casings which in turn leads to significant system and subsequent financial advantages during the production process.

Although specific embodiments have been illustrated and described herein, it will be appreciated by those of ordinary skill in the art that any arrangement that is calculated to achieve the same purpose may be substituted for the specific embodiments shown. Various embodiments use permutations and/or combinations of embodiments described herein. It is to be understood that the above description is intended to be illustrative, and not restrictive, and that the phraseology or terminology employed herein is for the purpose of description. Combinations of the above embodiments and other embodiments will be apparent to those of skill in the art upon studying the above description.

What is claimed is:

1. A method comprising:
   transmitting a plurality of electromagnetic signals in a multi-pipe structure, the electromagnetic signals having different frequencies, a different set of frequencies selected for a different pipe of the multi-pipe structure;
   estimating, under control of a processor, for each respective pipe of the multi-pipe structure, a defect in the respective pipe by:
   using a delta-like response for each pipe of the multi-pipe structure that is excited at the selected set of frequencies of the respective pipe;
   using an estimated defect of each pipe, other than the respective pipe, that is excited by the selected set of frequencies of the respective pipe; and
   using a received response from transmitting the electromagnetic signal at the selected set of frequencies of the respective pipe; and
   generating an image of the multi-pipe structure using the estimated defect in each pipe of the multi-pipe structure.

2. The method of claim 1, where the different frequencies are selected from the range between 0.1 Hz and 1000 Hz and at least one of the different frequencies used is sensitive mostly to the first pipe.

3. The method of claim 1, where estimating the defect in a pipe of the multi-pipe structure is derived by solving a linear system of equations that contains the delta-like responses of each pipe of the multi-pipe structure, and received responses measured in at least one receiver to the plurality of electromagnetic signals generated having at least two frequencies by at least one transmitter, where solving the linear system of equations includes solving by a least square method.

4. The method of claim 1, wherein estimating, for each respective pipe of the multi-pipe structure, the defect in the respective pipe includes estimating the defect for each respective pipe of the multi-pipe structure in ordered stages beginning with an innermost pipe and ending with an outermost pipe in an order based on a diameter of pipes of the multi-pipe structure and with each electromagnetic signal at its selected set of frequencies exciting only the pipe assigned to the selected set of frequencies and pipes having a smaller diameter than the pipe assigned to the selected set of frequencies, wherein averages of the selected sets of frequencies decrease in magnitude in order from an average of the selected set of frequencies assigned to the innermost pipe to an average of the selected set of frequencies assigned to the outermost pipe, wherein processing a first stage of the ordered stages to estimate the defect in the innermost pipe includes acquiring a response from the innermost pipe excited at the selected set of frequencies and applying an a priori calibrated delta-like response for a pipe with known dimensions and electrical properties substantially equal to the innermost pipe; and processing subsequent stages such that each stage k, k being an integer from 2 to a number of pipes of the multi-pipe structure, includes estimating defects on a $k^{th}$ pipe by acquiring responses of the pipes at the selected set of frequencies of the $k^{th}$ pipe and applying known properties of pipes 1 to k−1 of the multi-pipe structure from previous stages along with a priori calibrated delta-like response with known dimensions and electrical properties for pipes 1 to k−1 at the selected set of frequencies of the $k^{th}$ pipe.

5. The method of claim 1, wherein prior to estimating, for each respective pipe of the multi-pipe structure, a defect in the respective pipe, the method includes estimating permeability and conductivity of pipes of the multi-pipe structure, wherein estimating the conductivity and permeability of the pipes comprises:
   selecting a response from a precomputed library of calibrated responses; and
   performing an inversion on a non-defected section with nominal thickness of the multi-pipe structure.

6. The method of claim 5, wherein the method includes:
   acquiring data at multiple frequencies for non-defect sections of the pipes of the multi-pipe structure, the data at higher frequencies employed to estimate electrical property values for inner most pipes first;
   employing data at lower frequencies for non-defect sections of the pipes of the multi-pipe structure to estimate electrical property values for outer most pipes using electrical properties of inner pipes from employing the data at higher frequencies; and
   comparing data for each pipe, after processing with respect to other pipes of the multi-pipe structure, with responses in a database with known electrical property values for pipes having the same dimensions to estimate the electrical properties of the pipes of the multi-pipe structure.

7. The method of claim 5, wherein the method includes:
   acquiring data in a time domain from exciting the pipes of the multi-pipe structure, the data including a decay response of a sensor;
   dividing the decay response of the sensor into M sub-regions such that an effect of an $m^{th}$ pipe is being observed from a beginning of an $m^{th}$ sub-region; and
   processing values of the decay response at these sub-regions to estimate electrical properties of the pipes.

8. The method of claim 1, wherein the method includes receiving responses from selected ones of pipes of the multi-pipe structure by using receivers with variable sizes or numbers of turns, or by using transmitters with variable dimensions, variable current levels, or tapped transmitter coils to excite the selected ones of the pipe.

9. A machine-readable storage device having instructions stored thereon, which, when executed by one or more processors of a machine, cause the machine to perform operations, the operations comprising:
   transmitting a plurality of electromagnetic signals in a multi-pipe structure, the electromagnetic signals having different frequencies, a different set of frequencies selected for a different pipe of the multi-pipe structure;
   estimating, for each respective pipe of the multi-pipe structure, a defect in the respective pipe by:
      using a delta-like response for each pipe of the multi-pipe structure that is excited at the selected set of frequencies of the respective pipe;
      using an estimated defect of each pipe, other than the respective pipe, that is excited by the selected set of frequencies of the respective pipe; and
      using a received response from transmitting the electromagnetic signal at the selected set of frequencies of the respective pipe; and
   generating an image of the multi-pipe structure using the estimated defect in each pipe of the multi-pipe structure.

10. The machine-readable storage device of claim 9, wherein estimating, for each respective pipe of the multi-pipe structure, the defect in the respective pipe includes estimating the defect for each respective pipe of the multi-pipe structure in ordered stages beginning with an innermost pipe and ending with an outermost pipe in an order based on a diameter of pipes of the multi-pipe structure and with each electromagnetic signal at its selected set of frequencies exciting only the pipe assigned to the selected set of frequencies and pipes having a smaller diameter than the pipe assigned to the selected set of frequencies, wherein averages of the selected sets of frequencies decrease in magnitude in order from an average of the selected set of frequencies assigned to the innermost pipe to an average of the selected sets of frequencies assigned to the outermost pipe, wherein processing a first stage of the ordered stages to estimate the defect in the innermost pipe includes acquiring a response from the innermost pipe excited at the selected set of frequencies and applying an a priori calibrated delta-like response for a pipe with known dimensions and electrical properties substantially equal to the innermost pipe; and processing subsequent stages such that each stage k, k being an integer from 2 to a number of pipes of the multi-pipe structure, includes estimating defects on a $k^{th}$ pipe by acquiring responses of the pipes at the selected set of frequencies of the $k^{th}$ pipe and applying known properties of pipes 1 to k−1 of the multi-pipe structure from previous stages along with a priori calibrated delta-like response with known dimensions and electrical properties for pipes 1 to k−1 at the selected set of frequencies of the $k^{th}$ pipe.

11. The machine-readable storage device of claim 9, wherein the operations include,
   prior to estimating, for each respective pipe of the multi-pipe structure, a defect in the respective pipe, estimating permeability and conductivity of the pipes of the multi-pipe structure:
   acquiring data at multiple frequencies for non-defect sections of the pipes of the multi-pipe structure, the data at higher frequencies employed to estimate electrical property values for inner most pipes first;
   employing data at lower frequencies for non-defect sections of the pipes of the multi-pipe structure to estimate electrical property values for outer most pipes using electrical properties of inner pipes from employing the data at higher frequencies;
   comparing data for each pipe, after processing with respect to other pipes of the multi-pipe structure, with responses in a database with known electrical property values for pipes having same dimensions to estimate electrical properties of the pipes of the multi-pipe structure;
   acquiring data in a time domain from exciting the pipes of the multi-pipe structure, the data including a decay response of a sensor;
   dividing the decay response of the sensor into M sub-regions such that an effect of an $m^{th}$ pipe is being observed from a beginning of an $m^{th}$ sub-region; and
   processing values of the decay response at these sub-regions to estimate electrical properties of the pipes.

12. A system comprising:
   a set of transmitters arrangeable in a multi-pipe structure to transmit a plurality of electromagnetic signals in the multi-pipe structure;
   a set of receivers arrangeable in the multi-pipe structure to receive signals in response to exciting pipes in the multi-pipe structure, the set of receivers and/or the set of transmitters structured such that received responses are operatively received only from a selected pipe of the multi-pipe structure and from pipes interior to the selected pipe in the multi-pipe structure;

a processor arranged to estimate, for each respective pipe of the multi-pipe structure, a defect in the respective pipe by:
use of a delta-like response for each pipe of the multi-pipe structure that is excited at a selected set of frequencies of the respective pipe;
use of an estimated defect of each pipe, other than the respective pipe, that is excited by the selected set of frequencies of the respective pipe; and
use of a received response from transmission of the electromagnetic signal at the selected set of frequencies of the respective pipe; and
arranged to generate an image of the multi-pipe structure by use of the estimated defect in each pipe of the multi-pipe structure.

13. The system of claim 12, wherein the processor arranged to estimate, for each respective pipe of the multi-pipe structure, the defect in the respective pipe includes the processor arranged to estimate the defect for each respective pipe of the multi-pipe structure in ordered stages beginning with an innermost pipe and ending with an outermost pipe in an order based on a diameter of the pipes of the multi-pipe structure and with each electromagnetic signal at a selected set of frequencies exciting only the pipe assigned to the selected set of frequencies and pipes having a smaller diameter than the pipe assigned to the selected set of frequencies.

14. The system of claim 13, wherein averages of the selected sets of frequencies are larger in magnitude in order from an average of the selected set of frequencies assigned to the innermost pipe to an average of the selected set of frequencies assigned to the outermost pipe, wherein the processor is arranged to process a first stage of the ordered stages to estimate the defect in the innermost pipe with the processor arranged to acquire a response from the innermost pipe excited at the selected set of frequencies and apply an a priori calibrated delta-like response for a pipe with known electrical properties having dimensions substantially equal to the innermost pipe; and to process subsequent stages such that each stage k, k being an integer from 2 to a number of pipes of the multi-pipe structure, the processor is arranged to estimate defects on a $k^{th}$ pipe by acquisition of responses of the pipes at the selected set of frequencies of the $k^{th}$ pipe and application of known properties of pipes 1 to k−1 of the multi-pipe structure from previous stages along with a priori calibrated delta-like response with known dimensions and electrical properties for pipes 1 to k−1 at the selected set of frequencies of the $k^{th}$ pipe.

15. The system of claim 12, wherein the processor is arranged to estimate permeability and conductivity of the pipes of the multi-pipe structure, prior to the estimate, for each respective pipe of the multi-pipe structure, of a defect in the respective pipe.

16. The system of claim 15, wherein the processor is arranged to:
acquire data at multiple frequencies for non-defect sections of the pipes of the multi-pipe structure, data at higher frequencies utilized to estimate electrical property values for inner most pipes first;
employ data at lower frequencies for non-defect sections of the pipes of the multi-pipe structure to estimate electrical property values for outer most pipes by use of electrical properties of inner pipes from utilization of the data at higher frequencies; and
compare data for each pipe, after processing with respect to other pipes of the multi-pipe structure, with responses in a database with known electrical property values for pipes
having same dimensions to estimate electrical properties of the pipes of the multi-pipe structure.

17. The system of claim 15, wherein the processor is arranged to:
acquire data in a time domain from excitation of the pipes of the multi-pipe structure, the data including a decay response of a sensor;
divide the decay response of the sensor into M sub-regions such that an effect of an $m^{th}$ pipe is being observed from a beginning of an $m^{th}$ sub-region; and
process values of the decay response at these sub-regions to estimate electrical properties of the pipes.

18. The system of claim 15, wherein the set of receivers includes receivers with variable sizes or numbers of turns.

19. The system of claim 15, wherein the set of transmitters includes transmitters with variable dimensions or tapped transmitter coils to excite the selected pipe.

20. The system of claim 15, wherein the processor is arranged to control variable current levels to the set of transmitters to excite the selected pipe.

* * * * *